(12) United States Patent
Bertinetti et al.

(10) Patent No.: US 11,612,712 B2
(45) Date of Patent: Mar. 28, 2023

(54) MODULARIZED RESPIRATORY TREATMENT APPARATUS

(71) Applicant: ResMed Pty Ltd, Bella Vista (AU)

(72) Inventors: Mark Bertinetti, Hornsby (AU); Zhuo Ran Tang, Maroubra (AU); Craig Laing, Thornleigh (AU); Jing Wen Xie, Lindfield (AU); Jianhua Zhu, Carlingford (AU); Chinmayee Somaiya, Sydney (AU); Graham Stephen Cutcliffe, Sydney (AU); Sandra Robyn Curtis, Warrimoo (AU); Peter Milliken, West Hoxton (AU); Dimitri Marco Maurer, Umina (AU)

(73) Assignee: ResMed Pty Ltd

( * ) Notice: Subject to any disclaimer, the term of this patent is extended or adjusted under 35 U.S.C. 154(b) by 620 days.

(21) Appl. No.: 16/794,416

(22) Filed: Feb. 19, 2020

(65) Prior Publication Data

US 2020/0261682 A1   Aug. 20, 2020

Related U.S. Application Data

(62) Division of application No. 15/042,335, filed on Feb. 12, 2016, now Pat. No. 10,596,341, which is a
(Continued)

(51) Int. Cl.
*A61M 16/08* (2006.01)
*A61M 16/00* (2006.01)
(Continued)

(52) U.S. Cl.
CPC .... *A61M 16/0816* (2013.01); *A61M 16/0051* (2013.01); *A61M 16/0066* (2013.01);
(Continued)

(58) Field of Classification Search
CPC .... E05B 61/00; E05B 65/00; A61M 16/0051; A61M 16/0816; A61M 16/0841–0858; A61M 2016/0015–0042
See application file for complete search history.

(56) References Cited

U.S. PATENT DOCUMENTS

| 3,595,228 A | 7/1971 | Simon et al. |
| 4,148,313 A | 4/1979 | Bird et al. |

(Continued)

FOREIGN PATENT DOCUMENTS

| WO | 2004043528 A1 | 5/2004 |
| WO | 2007019628 A1 | 2/2007 |

(Continued)

*Primary Examiner* — Valerie L Woodward
(74) *Attorney, Agent, or Firm* — Botos Churchill IP Law LLP

(57) ABSTRACT

A modularized respiratory treatment apparatus provides various respiratory pressure treatments. The apparatus may be formed by discrete connectable modules such as a flow generator module, alarm module and/or humidifier module. Each module may include its own external casing or housing to independently retain or enclose the respective components that serve the function of the module. Different modules may be adapted with different components and functionalities and may be readily coupled using standardized gas and electrical connection configurations that have flow and communication paths that extend through the modules. When coupled, operation of the respiratory treatment apparatus may be controlled by detection of different modules, such as the alarm module that generates visual and/or audible alarms based on detected conditions, so as to selectively enable or disable different respiratory treatments. The discrete modules of the medical treatment apparatus may include tamper resistant locking mechanisms to impede unauthorized separation of some modules.

8 Claims, 13 Drawing Sheets

Related U.S. Application Data division of application No. 13/608,293, filed on Sep. 10, 2012, now Pat. No. 9,302,066.

(60) Provisional application No. 62/533,431, filed on Sep. 12, 2011.

(51) Int. Cl.
*E05B 61/00* (2006.01)
*E05B 65/00* (2006.01)
*E05B 17/20* (2006.01)
*A61M 16/10* (2006.01)
*A61M 16/16* (2006.01)

(52) U.S. Cl.
CPC ...... *A61M 16/0069* (2014.02); *A61M 16/024* (2017.08); *E05B 17/2057* (2013.01); *E05B 61/00* (2013.01); *E05B 65/00* (2013.01); *A61M 16/107* (2014.02); *A61M 16/1075* (2013.01); *A61M 16/16* (2013.01); *A61M 2016/0027* (2013.01); *A61M 2016/0039* (2013.01); *A61M 2205/3334* (2013.01); *A61M 2205/3365* (2013.01); *A61M 2205/3375* (2013.01); *A61M 2205/50* (2013.01); *A61M 2205/502* (2013.01); *A61M 2205/581* (2013.01); *A61M 2205/583* (2013.01); *A61M 2230/205* (2013.01); *Y10T 292/1033* (2015.04)

(56) References Cited

U.S. PATENT DOCUMENTS

| | | |
|---|---|---|
| 4,619,269 A | 10/1986 | Cutler et al. |
| 4,944,310 A | 7/1990 | Sullivan |
| 4,990,894 A | 2/1991 | Loescher et al. |
| 5,485,850 A | 1/1996 | Dietz |
| 5,542,287 A | 8/1996 | Powers |
| 6,910,481 B2 | 6/2005 | Kimmel et al. |
| 7,080,645 B2 | 7/2006 | Genger et al. |
| 7,096,865 B1 | 8/2006 | Coury et al. |
| 7,314,046 B2 | 1/2008 | Schroeder et al. |
| 8,469,026 B2 | 6/2013 | Blomberg et al. |
| 2003/0188748 A1 | 10/2003 | Sinderby et al. |
| 2007/0169776 A1* | 7/2007 | Kepler ............. A61M 16/107 128/200.14 |
| 2008/0072900 A1* | 3/2008 | Kenyon ............ A61M 16/024 128/204.18 |
| 2008/0097168 A1 | 4/2008 | Hopermann et al. |
| 2008/0264413 A1* | 10/2008 | Doherty ........... A61M 16/0825 128/202.27 |
| 2009/0020120 A1 | 1/2009 | Schatzl et al. |
| 2011/0155132 A1 | 6/2011 | Virr et al. |
| 2011/0162647 A1 | 7/2011 | Hubby et al. |
| 2011/0313689 A1 | 12/2011 | Holley et al. |

FOREIGN PATENT DOCUMENTS

| | | | |
|---|---|---|---|
| WO | 2010028427 A1 | 3/2010 | |
| WO | WO-2010031126 A1 * | 3/2010 | ........ A61M 16/0066 |

\* cited by examiner

MODULARIZED RESPIRATORY TREATMENT APPARATUS

CROSS REFERENCE TO RELATED APPLICATIONS

This application is a divisional of U.S. application Ser. No. 15/042,335 filed on Feb. 12, 2016, which is a divisional of U.S. application Ser. No. 13/608,293 filed on Sep. 10, 2012, now U.S. Pat. No. 9,302,066, which claims the benefit of the filing date of U.S. Provisional Patent Application No. 61/533,431 filed Sep. 12, 2011, all of which are incorporated herein by reference.

FIELD OF THE TECHNOLOGY

The present technology relates to apparatus for treatment of respiratory conditions such as pressure treatment apparatus for conditions related to obstructive sleep apnea (OSA), central sleep apnea (CSA), sleep disordered breathing (SDB), Cheyne-Stokes respiration (CSR) allergy induced upper airway obstruction, early viral infection of the upper airway, respiratory insufficiency etc. More particularly, the technology involves modularization of the components for such respiratory treatment apparatus.

BACKGROUND OF THE TECHNOLOGY

Sleep is important for good health. Frequent disturbances during sleep or sleep fragmentation can have severe consequences including day-time sleepiness (with the attendant possibility of motor-vehicle accidents), poor mentation, memory problems, depression and hypertension. For example, a person with nasal congestion may snore to a point that it disturbs that person's ability to sleep. Similarly, people with OSA are also likely to disturb their partner's sleep. One form of treatment for patients with OSA is continuous positive airway pressure (CPAP) applied by a flow generator such as a blower (compressor) via a connecting delivery hose with a patient interface. Such a pressure treatment may be adjusted in response to detected patient conditions such as apneas, snoring or hypopneas but generally maintains an approximately constant positive pressure during each breathing cycle of the patient. The positive pressure can prevent a collapse of the patient's airway during inspiration, thus preventing events such as snoring, apneas or hypopneas and their sequelae.

Respiratory treatment apparatus may include a flow generator, an air filter, a patient interface such as a mask or cannula, an air delivery conduit connecting the flow generator to the mask, various sensors and a microprocessor-based controller. The flow generator may include a servo-controlled motor and an impeller. The flow generator may also include a valve capable of discharging air to atmosphere as a means for altering the pressure delivered to the patient as an alternative to motor speed control. The sensors may measure, amongst other things, motor speed, gas volumetric flow rate and outlet pressure, such as with a pressure transducer, flow sensor or the like. The apparatus may optionally include a humidifier and/or heater elements in the path of the air delivery circuit. The controller may include data storage capacity with or without integrated data retrieval/transfer and display functions.

Positive airway pressure may be delivered in many forms. As previously mentioned, a CPAP treatment may maintain a treatment pressure across the inspiratory and expiratory levels of the patient's breathing cycle at an approximately constant level. Alternatively, pressure levels may be adjusted to change synchronously with the patient's breathing cycle. For example, pressure may be set at one level during inspiration and another lower level during expiration for patient comfort. Such a pressure treatment system may be referred to as bi-level. Alternatively, the pressure levels may be continuously adjusted to smoothly replicate changes in the patient's breathing cycle. A pressure setting during expiration lower than inspiration may generally be referred to as expiratory pressure relief. As described by Sullivan in U.S. Pat. No. 4,944,310, positive airway pressure treatments typically provide gas under pressures to the patient in the range of 4 to 15 $cmH_2O$ from the device and may involve flow rates of at about 120 liters/minute. Some of the air may escape via an end restriction and not be delivered to the patient. These pressure settings may also be adjusted based on the detection of conditions of the patient's airway or respiration. For example, treatment pressure may be increased in the detection of partial obstruction, apnea or snoring. In some cases, positive airway pressure may be adapted to provide ventilation support. For example, a patient's ventilatory needs may be supported on a breath-by-breath basis by automatically calculating a target ventilation and adjusting the pressure support generated by an apparatus, such as a bi-level pressure treatment apparatus, so as to achieve the target ventilation.

Other devices are known for providing respiratory tract therapy. For example, Schroeder et al. describes an apparatus for delivering heated and humidified air to the respiratory tract of a human patient in U.S. Pat. No. 7,314,046, which was filed on 8 Dec. 2000 and assigned to Vapotherm Inc. Similarly, Genger et al. discloses an anti-snoring device with a compressor and a nasal air cannula in U.S. Pat. No. 7,080,645, filed 21 Jul. 2003 and assigned to Seleon GmbH.

Respiratory treatment apparatus are sometimes provided with accessory components for comfort conditioning of the flow or pressurized air supplied by the flow generator. For example, the supplied air may be applied to a humidifier to humidify and warm the treatment gas prior to its delivery to a patient. Similarly, various heating elements can be connected with a delivery conduit to help in maintaining a particular temperature of the supplied gas as it is conducted to the patient from a supply unit or humidifier.

It may be desirable to develop these devices with improved design efficiencies.

SUMMARY OF THE TECHNOLOGY

In an aspect of the present technology, apparatus and methods provide respiratory treatment for a patient.

In another aspect of the present technology, a respiratory treatment apparatus is formed by separable modules each with its own external casing or housing.

Another aspect of one form of the present technology is a system comprising a first module that is constructed and arranged to provide Positive Airway Pressure (PAP) therapy, and a second module that is constructed and arranged to provide mitigation in the event of an alarm condition being fulfilled with respect to the therapy in use. In one form, the two modules may be physically connected. In one form, the second module may be in data communication with the first module, without being physically connected, and nevertheless provide alarm functionality.

Another aspect of the present technology is a tamper resistant respiratory apparatus.

In another aspect of the technology, a respiratory treatment apparatus includes a separable alarm module, a separable flow generator module and a separable humidifier module. Such a separable design may be, from the perspective of the ordinary user, a permanent attachment or at least an attachment that is difficult for such a user to detach. However, it may be readily separable by a trained technician for service or replacement. Nevertheless, the design can provide a very easy to attach module that simplifies upgrading of a flow generator or other respiratory apparatus so as to add an additional functionality, such as an alarm functionality.

Another aspect of the present technology is a system comprising respiratory treatment apparatus and a module that is connectable to and removable from the respiratory treatment apparatus via a latching mechanism, wherein the latching mechanism has an associated connection step and a removing step that is not a reversal of the connection step. Another aspect of the present technology is a process of assembly of a module to a respiratory apparatus, and a process of removal of the module from the respiratory apparatus. In one form, the process of removal of the module comprises additional or alternative steps to the process of assembly of the module.

In some embodiments, the technology involves an alarm module for coupling with a respiratory treatment apparatus. The respiratory treatment apparatus may be configured to generate a respiratory pressure treatment. The alarm module may include a breathable gas flow channel. The channel may include an inlet coupling and outlet coupling such that the inlet coupling is adapted to couple with a breathable gas flow output of a respiratory treatment apparatus. The alarm module may also include an alarm component. The module may further include an electrical coupler that is adapted for electrical communication between the alarm component and a controller of the respiratory treatment apparatus. The alarm module may also include a modularized housing configured to retain the channel and the alarm component. The modularized housing may be adapted for removable coupling with a housing of the respiratory treatment apparatus.

In some embodiments, the apparatus may also include an alarm controller including at least one processor. The processor may be configured for activating an alarm associated with operation of the respiratory treatment apparatus. The controller may be retained by the modularized housing. In some cases, the alarm module may include a speaker, wherein the alarm controller is coupled to the speaker and adapted to produce the alarm as an audible sound, and wherein the speaker is retained by the modularized housing. The alarm module may also include a set of lights, wherein the alarm controller is coupled to the set of lights and configured to produce the alarm as a visual warning, and wherein the set of lights is retained by the modularized housing.

One aspect of one form of the present technology is the use of a loudspeaker as an alarm output device.

Another aspect of one form of the present technology is a high efficiency audio driver, preferably a switching mode audio driver, preferably a class D audio amplifier, which may drive the speaker.

Another aspect of one form of the present technology is an electrical sub-system that uses frequency synthesizing to achieve an alarm spectrum.

In some cases, the alarm module may also include a pressure sensor to sense a pressure of the breathable gas of the channel, wherein the alarm controller is coupled to the sensor and configured to produce the alarm based on a signal of the pressure sensor, and wherein the pressure sensor is retained by the modularized housing. The alarm module may also include a microphone to sense ambient noise, wherein the alarm controller is coupled to the microphone and configured to produce the alarm based on a signal of the microphone, and wherein the microphone is retained by the modularized housing.

Optionally, the modularized housing may include a locking mechanism for releasably locking the modularized housing in a coupling arrangement with the housing of the respiratory treatment apparatus. The locking mechanism may include a set of latches. The set of latches may be coupled with a spring. The modularized housing may also include an access aperture for releasing the set of latches. The locking mechanism may also include a securing screw, the securing screw comprising first and second thread sections, the second thread sections configured for threaded attachment to a screw hole of the set of latches for retaining the locking mechanism in a locked arrangement. Optionally, the securing screw may include an unthreaded shaft portion between the first and second threaded sections, the unthreaded shaft portion being configured to slideably traverse within the screw hole of the set of latches for releasing the locking mechanism from a locked arrangement. In one form, the securing screw has a double start thread. In another form, the securing screw has a three or more start thread.

In some cases, the alarm module may also include a further electrical coupler, the further coupler adapted for electrical communication between the controller of the respiratory treatment apparatus and a controller of a humidifier module for the respiratory treatment apparatus. In some such cases, the alarm module may also include a further locking mechanism for releasably locking the modularized housing in a coupling arrangement with a housing of a modularized humidification module for the respiratory treatment apparatus. Optionally, the outlet coupling of the alarm module may be adapted for engagement with a breathable gas input to the humidification module. The further locking mechanism may comprise a set of apertures of the modularized housing configured to releasably engage with a set of latches of a housing of the modularized humidification module.

Some embodiments of the present technology may involve a system for respiratory pressure treatment. The system may include a respiratory pressure treatment module having a flow generator, the respiratory pressure treatment module including a controller, with at least one processor, the controller configured to control the flow generator to generate a pressure treatment to a patient interface according to first and second pressure therapy regimes, wherein the controller is configured to enable the first pressure therapy regime and disable the second pressure therapy regime in the absence of a detection by the controller of an alarms module. In some cases, the controller of the respiratory pressure treatment module may be configured to enable the second pressure therapy regime based on a detection by the controller of a presence of the alarms module.

Optionally, the alarms module of the system may include a breathable gas flow channel including an inlet coupling and outlet coupling, the inlet coupling adapted to couple with a breathable gas flow output of the respiratory pressure treatment module. It may also include an alarm controller having at least one processor, the processor configured for activating an alarm associated with operation of the respiratory pressure treatment module. The module may also have an electrical coupler, the coupler adapted for electrical communication between the alarm controller and a controller of the respiratory treatment apparatus; and a modularized housing configured to retain the channel and the alarm controller, the modularized housing adapted for removable coupling with a housing of the respiratory pressure treatment module.

In some cases, the first pressure therapy regime may include a continuous positive airway pressure treatment. The second pressure therapy regime may include a pressure support ventilation.

Some embodiments of the present technology may involve a method for selectively activating a pressure therapy regime in a pressure treatment apparatus. The method may be executed by a processor of a flow generator module of a pressure treatment apparatus. The method may involve detecting a presence or absence of a coupled alarms module, the alarms module being adapted for releasable coupling with the flow generator module. The method may also involve selecting a pressure therapy regime from a plurality of distinct pressure therapy regimes based on the detection of a presence or absence of the alarms module. The method may also involve controlling a generation of a flow of breathable gas according to the selected pressure therapy regime. In some cases, a first pressure therapy regime of the plurality of distinct pressure therapy regimes may involve a CPAP treatment. The first pressure therapy regime may be selected with processor in the absence of the detection of the alarms module. In some such cases, a second pressure therapy regime may be disabled by the processor in the absence of the detection of the alarms module. Optionally, a second pressure therapy regime of the plurality of distinct pressure therapy regimes comprises bi-level pressure support ventilation. Optionally, the second pressure therapy regime may be selected with the processor in the presence of the detection of the alarms module.

Another embodiment of the present technology may involve a tamper resistant locking mechanism for releasably coupling discrete modules of a treatment apparatus. The locking mechanism may include a movable latching portion, the movable latching portion being adapted for engagement with engagement apertures of a first housing structure. It may also include a securing shaft configured to secure the latching portion, the securing shaft comprising first and second sets of threads and an unthreaded shaft portion, the first and second sets of threads being separated by the unthreaded shaft portion.

In some such cases, the latching portion may include a threaded aperture for the securing shaft. The latching portion may be adapted to be secured against a second housing structure by coupling the second set of threads and threaded aperture so as to prevent displacement of the latching portion from the engagement apertures. Optionally, the threaded aperture of the latching portion may be adapted for slideable engagement with the unthreaded portion of the securing shaft to permit the latching portion to be moved for releasing and catching the latching portion. In some cases, the second housing structure may include a release aperture, the release aperture positioned and sized to selectively permit access to the latching portion to displace the latching portion for releasing the latching portion from the engagement apertures.

Optionally, the second housing structure may include a shaft aperture for receiving the securing shaft and engaging the securing shaft when the latching portion is secured against the second housing structure with the second set of threads of the securing shaft. The locking mechanism may also include a security label to conceal the shaft aperture. In some cases, the securing shaft may comprise a screw. Also, the first housing structure may include a housing to retain a flow generator of a respiratory treatment apparatus and wherein the second housing structure comprises a housing to retain an alarms module for the respiratory treatment apparatus.

Further embodiments and features of the present technology will be apparent from the following detailed disclosure, abstract, drawings and the claims.

BRIEF DESCRIPTION OF DRAWINGS

The present technology is illustrated by way of example, and not by way of limitation, in the figures of the accompanying drawings, in which like reference numerals refer to similar elements including.

DETAILED DESCRIPTION

Figure 1:
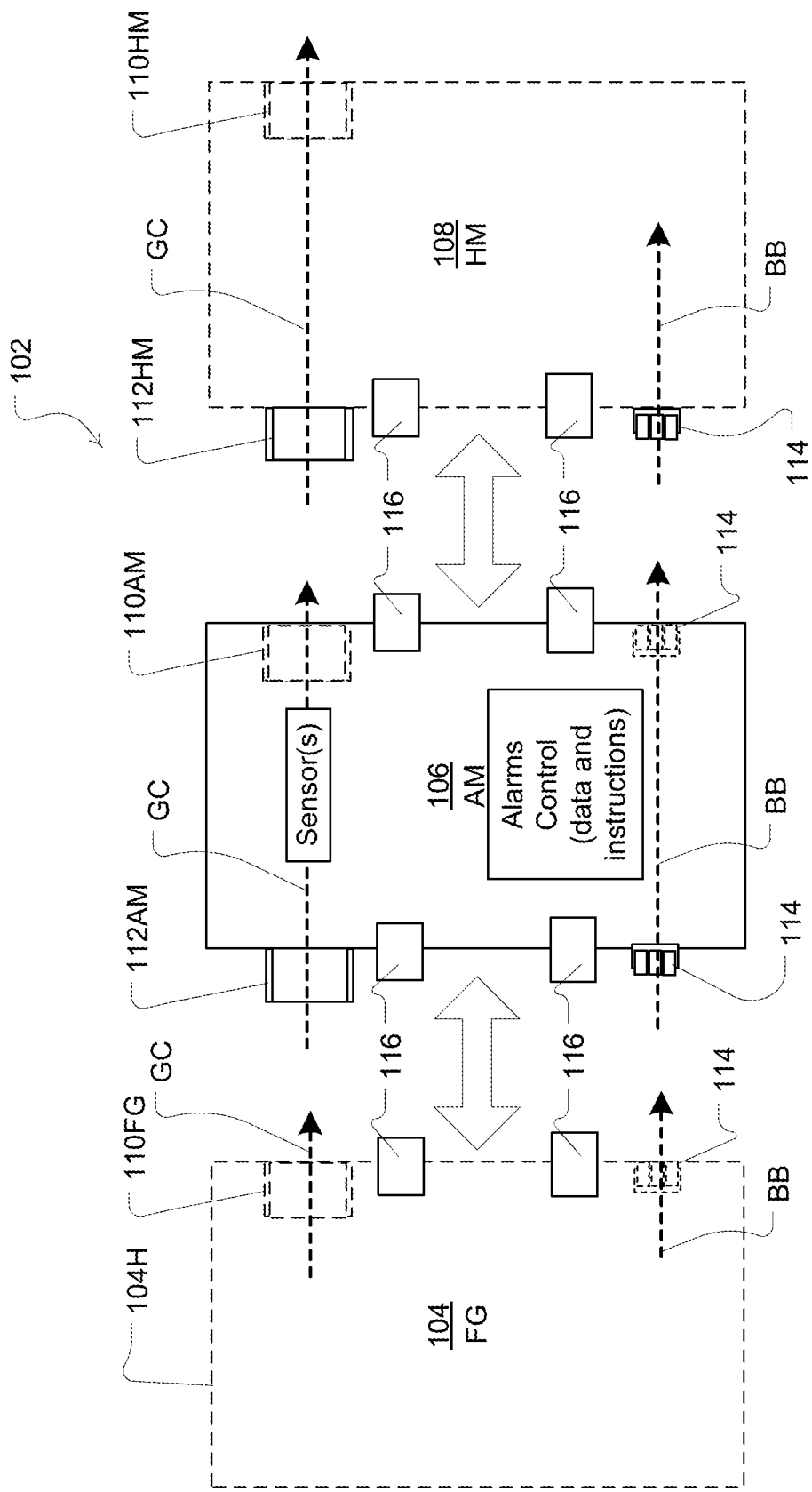
FIG. 1 is a schematic diagram of example modules with components of an apparatus for respiratory treatment in some embodiments of the present technology.
Figure 2:
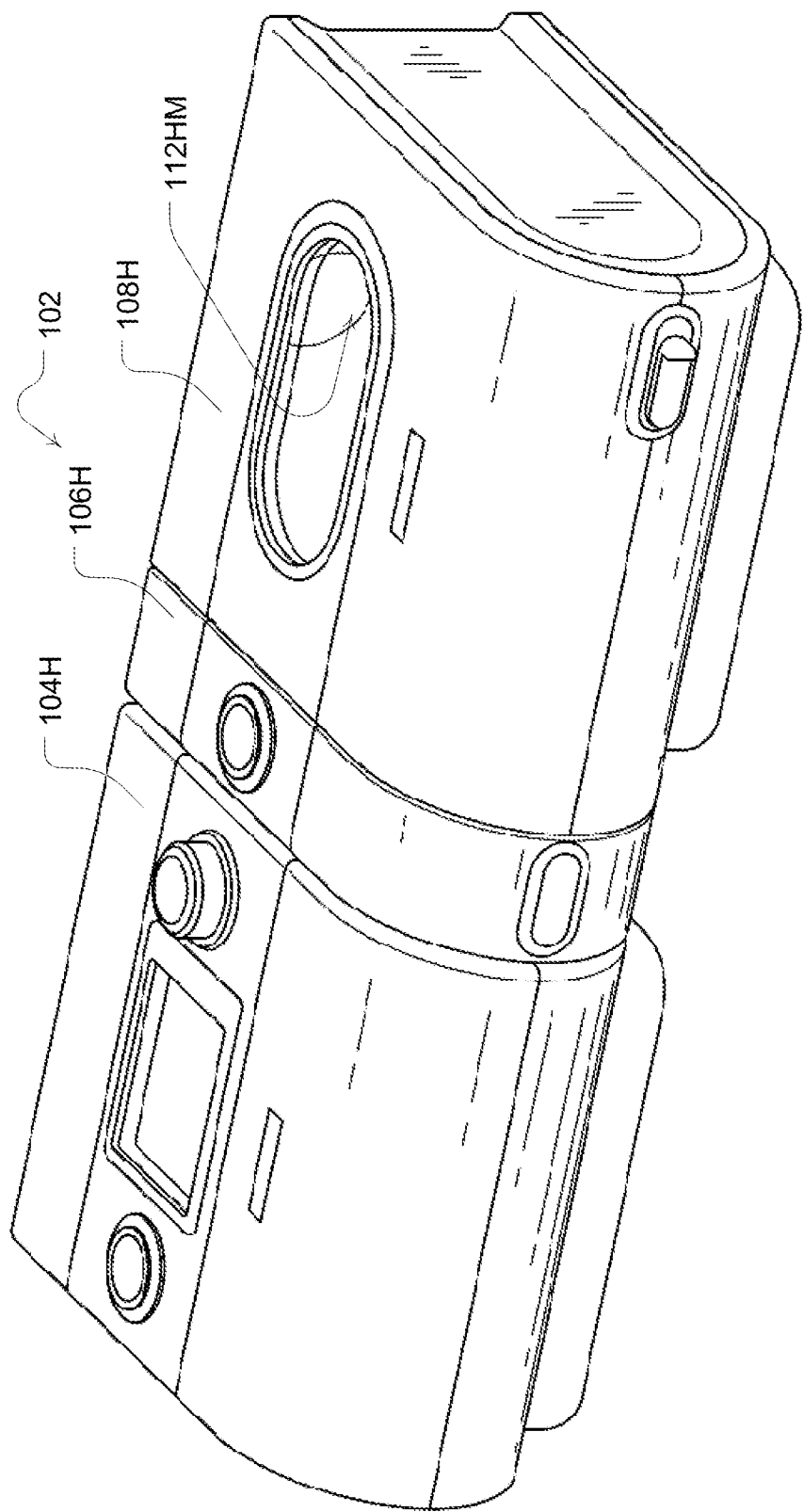
FIG. 2 illustrates an embodiment of a modularized respiratory treatment apparatus having a flow generator module, alarm module and humidifier module in a side-by-side coupled arrangement.
Figure 3:
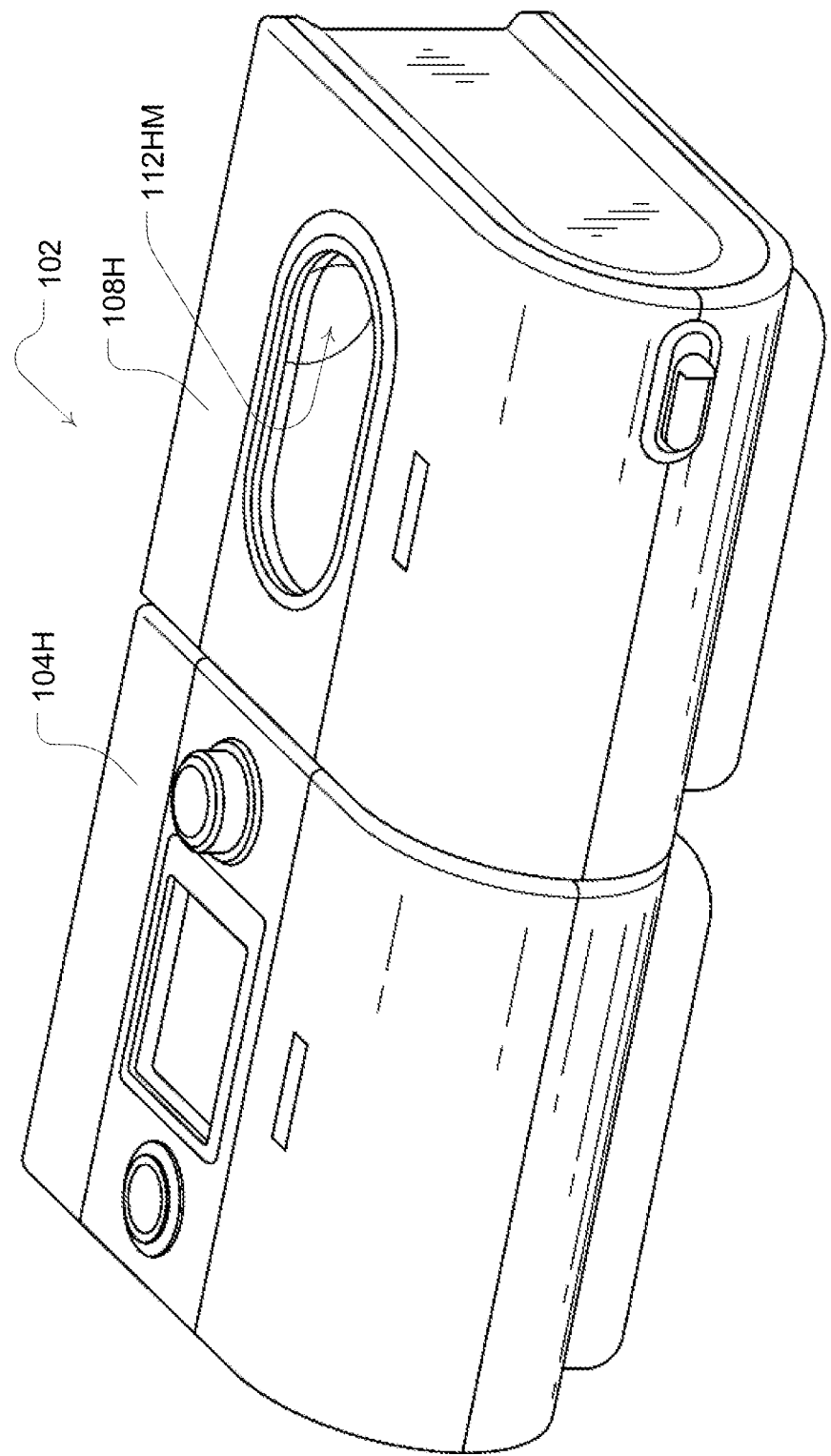
FIG. 3 illustrates another embodiment of the modularized respiratory treatment apparatus having a flow generator module and humidifier module in a side-by-side coupled arrangement.
Figure 4:
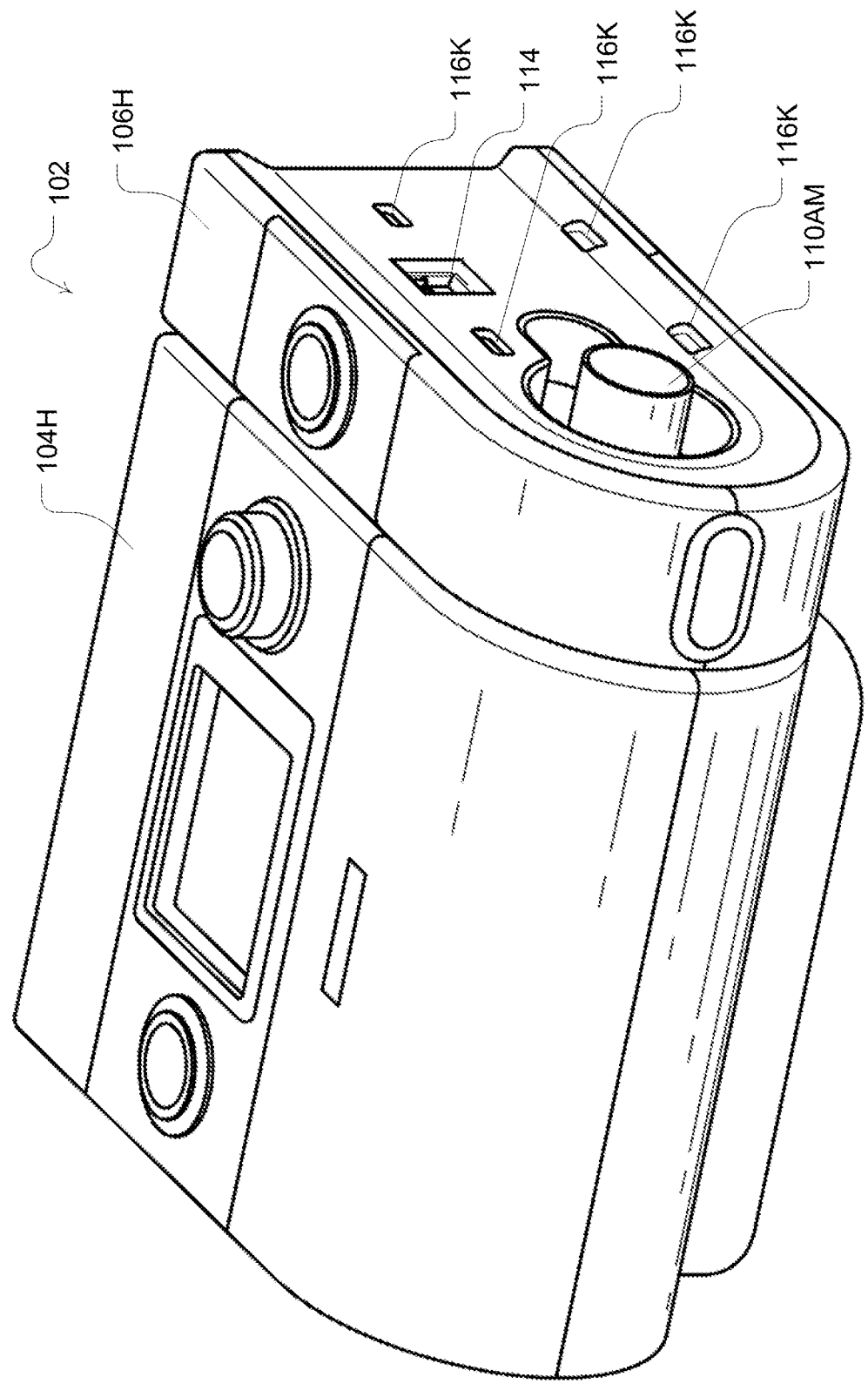
FIG. 4 illustrates another embodiment of the modularized respiratory treatment apparatus having a flow generator module and alarm module in a side-by-side coupled arrangement.
Figure 5:
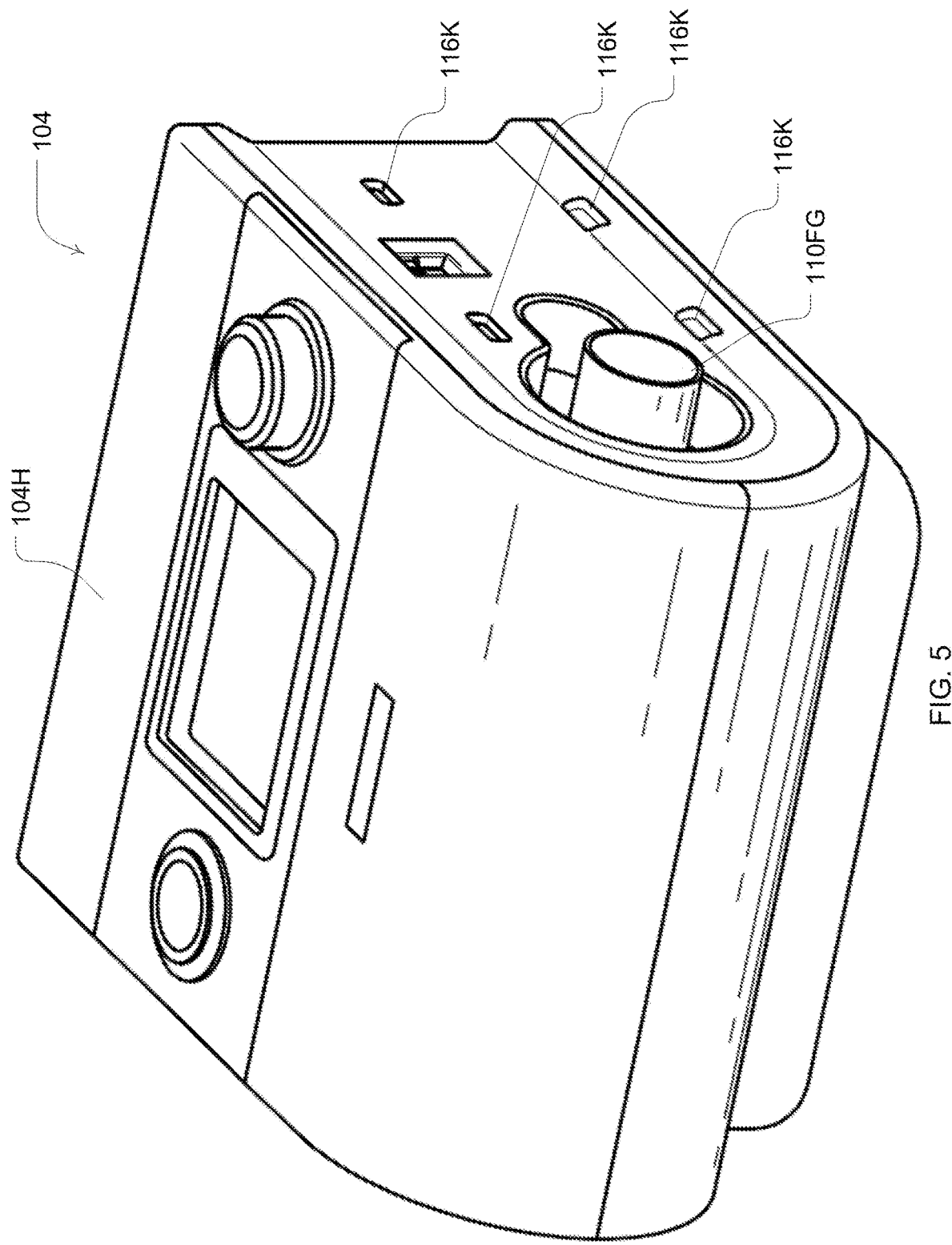
FIG. 5 illustrates another embodiment of the modularized respiratory treatment apparatus having only a flow generator module.
Figure 6B:
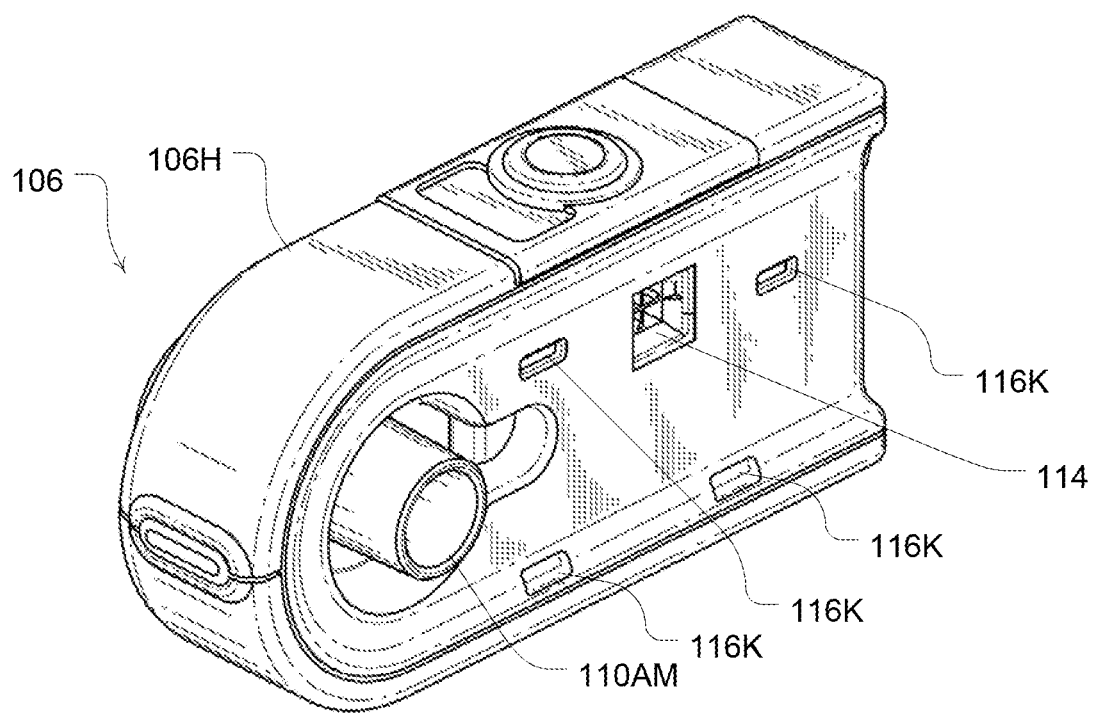
FIGS. 6A and 6B contain left and right side views that illustrate an embodiment of a modularized alarm module of the present technology.
Figure 6A:
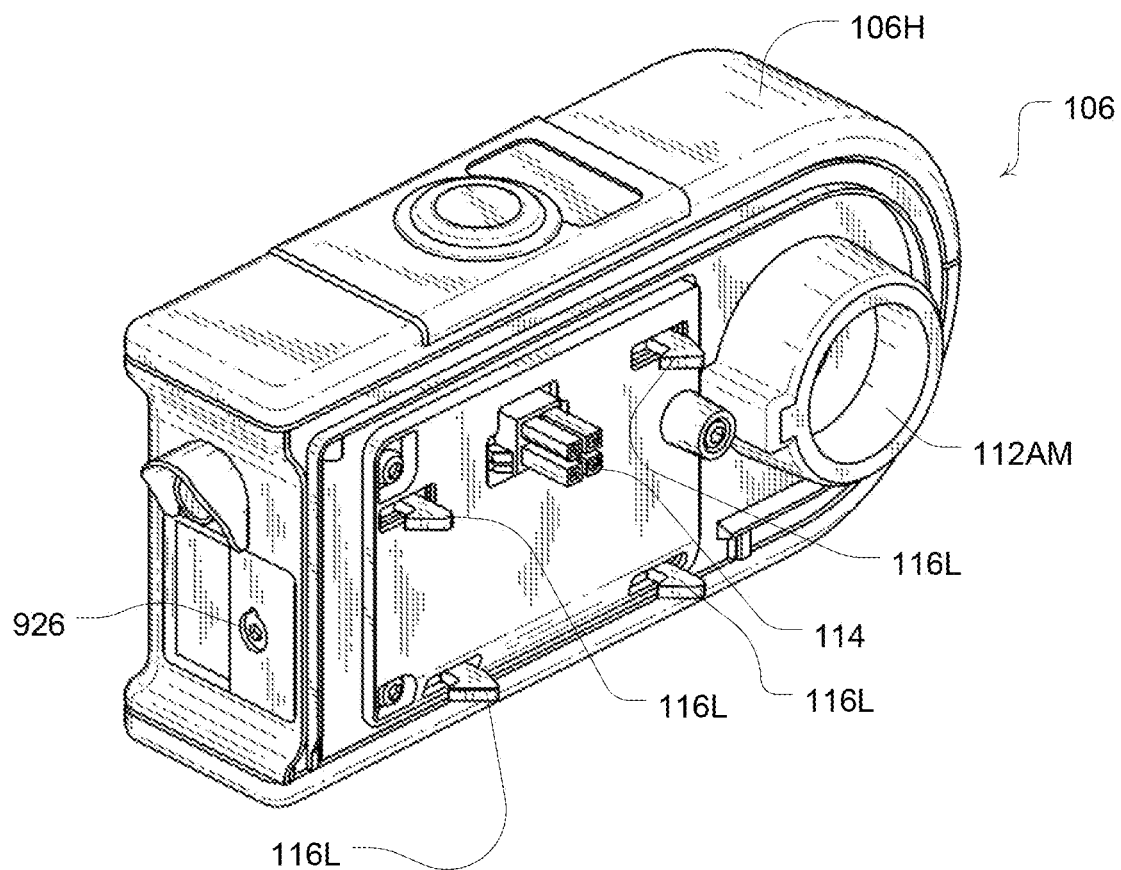

Embodiments of the present technology may be useful for implementation as a respiratory treatment apparatus 102 that may be formed by some or all of the modules illustrated in FIGS. 1 to 6. For example, the respiratory treatment apparatus 102 may be formed by a system of modules, each with housings that independently retain the respective components that serve the function(s) of the individual modules. Desirably, each module may be adapted with different components and functionalities and may be easily coupled together depending on the desired functionality of the respiratory treatment apparatus. Thus, when so coupled, the operation of the respiratory treatment apparatus 102 may be dictated based on the presence or absence of the different modules that may be detected. The modules may be coupled in a horizontal or side-by-side assembly as illustrated in FIGS. 2-4. However, other assembly orientations may be adapted. For example, a vertical or stacking of modules may also be adopted.

In one form of the present technology, a first printed circuit board (PCB) is constructed to provide therapy functionality, for example a pressure controller, under the control of a controller that is programmed to control delivery of one or more therapeutic regimes. Furthermore, a second, separate PCB is manufactured that is constructed and arranged to provide mitigation actions, for example the signaling of an alarm condition in the event of a low power situation. In use, while a module including only the first PCB has the capability of providing certain therapies, the module will not do so, or will only permit a subset of such therapies, unless a second module containing the second PCB is in data communication with the first module. The data communication may be wireless, but preferably wired.

As illustrated in the example of FIG. 1, the respiratory treatment apparatus may include a system formed by one or more of a flow generator module 104, an alarm module 106 and/or a humidifier module 108. Each module includes the components for its modularized functionality. Depending on the presence or absence of the alarm module and/or humidifier module, the flow generator may operate differently.

For example, an alarm module may generally include components and functionality for generating different types of alarms associated with the operations of the flow generator as discussed in more detail herein. The presence of an alarm module, or particular type of alarm module, can then permit the flow generator to deliver different treatments depending on its participation in the operation of the apparatus. For example, in some embodiments, without coupling with an alarm module, the flow generator may be enabled for certain pressure treatment regimes, such as a CPAP treatment, and not others, such as a pressure support ventilation treatment, even though the control programming for each of these different pressure treatment regimes is present in the flow generator module. In such a case, certain pressure treatment regimes may be disabled in the absence of any necessary module such as the alarm module. However, when a particular module, such as an alarms module, is coupled to the system, the flow generator may then be enabled to operate with the further pressure treatment regimes.

For example, by detecting the alarm module, different pressure treatment regimes that may be associated with a need for the alarm module may be activated by a controller of the flow generator. Such a detection and activation may be fully automated in conjunction with the controllers of the flow generator module and alarms module. Alternatively, it may be partially automated such as by permitting an authorized person to select and activate a pressure treatment regime when the added module has been detected by a controller of the flow generator. Similarly, removing of such an alarm module may then disable any pressure therapy regime of the flow generator that may be associated with the removed module. Thus, the flow generator may include programming that serves a safety function to permit enabling or disabling of different pressure treatment regimes depending on the need for certain functionality of other modules in the control of the particular pressure treatment regime.

Accordingly, in some embodiments, the flow generator module may typically include a flow generator housing 104H so as to retain components that may be involved in the generation of a pressure treatment according to one or more pressure treatment regimes. Typically such a module will include a flow generator such as a servo-controlled blower with an air inlet and impeller driven by a motor and a programmable controller for controlling the blower. Optionally, the air inlet may be coupled with a gas supply, such as for oxygen, to mix with or supplement the breathable gas supplied by the impeller to the airway of a user. Moreover, an air filter may be provided, such as a HEPA filter, to remove dust or other allergens from the air drawn into the air inlet. The flow generator may optionally be configured for generating pressure treatment depending on the enabled type of pressure treatment regime (e.g., continuous level, bi-level, varying level, pressure support etc.) and it may further be adjusted based on respiratory conditions (e.g., central or obstructive apnea, hypopnea, Cheyne-Stokes breathing, inadequate ventilation, etc.) that may be detected by the apparatus. Optionally such a module may also include a pressure sensor and/or flow sensor for controlling the blower and/or detecting conditions associated with patient's use of the device.

The controller or processor of the flow generator module 104 is typically configured and adapted to implement the control methodologies such as the methods and algorithms described herein. Thus, the controller may include integrated chips, a memory and/or processor control instructions or data in an information storage medium. For example, programmed instructions encompassing the control methodology may be coded on integrated chips in the circuits or memory of the device or such instructions may be loaded as software or firmware using an appropriate medium. With such a controller or processor, the apparatus can configured with the different pressure treatment regimes by including different pressure delivery equations that are used to set the speed or pressure of the blower or the exhaust venting by the release valve. The controller may enable or disable some treatment regimes based on the detection of the presence of some module (e.g., an alarm module) that may be required for the particular pressure treatment regime. Similarly, it may enable or disable some treatment regimes based on the absence of some module. In one form, the controller may be configured to control disabling of all treatment functionality if an alarm module is connected (e.g., it was detected previously or in a previous session) and then removed (e.g., it is not subsequently again detected). This control feature may thus disable functionality that may have been available and operable prior to the detection of the connection of the alarm module.

The flow generator module 104 may also typically be adapted to couple with a patient interface such as a flow delivery conduit and a mask or nasal prongs or nasal cannula, etc. to carry a flow of air or breathable gas to a patient's airway. In this way it may deliver a pressure treatment generated by the flow generator.

The flow generator module may couple with the patient interface either directly or through one or more other modules. To this end, the flow generator housing 104H may include a breathable gas output coupling 110FG. The outlet or output coupling may be adapted for connection to the tubing of a patient interface or an inlet or input coupling of another module, such as an input gas coupling 112AM of the alarm module or the input gas coupling 112HM of a humidifier housing 108H of humidifier module 108. Similarly, each module may have an outlet or output breathable gas coupling such as breathable gas output coupling 110AM of the alarm module and output coupling 110HM of the humidifier module. In this way, a breathable gas channel (illustrated in FIG. 1 as line "GC") from the flow generator may be formed by and extend through one or more modules to the patient interface from the flow generator module.

Optionally, a module of the system, such as the flow generator module may couple to a further sensor module such as a pulse oximeter module. For example, the pulse oximeter module may have a housing that attaches to the housing of the flow generator module. The pulse oximeter may optionally measure blood gas, such as with a finger sensor. The pulse oximeter module then may be configured to communicate information with the flow generator module, such as detected blood gas data or other conditions associated with a pulse oximeter.

Accordingly, the modules of the system may also have one or more electrical coupler(s) 114 for coupling the modules together for distributing power, such as from a shared power supply, and/or for communications between the modules of the system. Thus, the coupler may include one or more wires to a bus such as the bus described in U.S. patent application Ser. No. 13/060,566 and PCT/AU2009/001168, the entire disclosures of which are incorporated herein by reference. In such embodiments, the modules may each have a signal interface for a processor of the module for receiving and transmitting signals on the bus.

Thus, as illustrated in FIG. 1, a module, such as the alarm module, may have multiple couplers to permit a common bus to be expanded through one or more modules. In this regard, communication signals from or to an outer module, such as the humidifier, may pass through other modules, such as the alarm module, to permit communication with a base module, such as the flow generator. For example in some embodiments of such a system, the flow generator module may communicate through the alarm module to the humidifier module. Optionally, in some embodiments of such a system, the flow generator module may communicate through the humidifier module to the alarm module. Communications through additional modules may also be implemented.

The structure of each module's housing can provide a basis for standardizing an attachment configuration for self-alignment of the electrical and gas flow connections of the modules. In this regard, the connections may be structured as a portion of each housing, and may do so without flexible hoses or cables, to permit a simplified attachment of each connection. For example, with such self-aligning connections, by aligning the housings of two modules for connection, this may also serve to align the couplings and couplers for attachment. Thus, when the housings are aligned for connection, the flow couplings and the electrical couplers are thereby aligned so as to permit them both to be connected to their respective ports on each module simply by pushing the modules together. In such a case, it would not be necessary to separately connect the gas channel couplings and the electrical couplers. By keeping such a uniform connection structure (e.g., the distances between the gas connections and the electrical connections, their size and positioning on the housing) across different types of modules, it can simplify the use of different types of modules with a base module that may be the flow generator.

In this regard, and as illustrated in FIG. 1, the distance between the input connections (e.g., the gas connection and the electrical connection) as well as their size and positioning on both the alarm module and the humidifier module may be the same for each module to permit either to be connected directly to the flow generator when it is serving as the base module. Similarly, the distance between the output connections (e.g., the gas connection and the electrical connections) as well as their size and positioning on both the alarm module and the flow generator module may be the same for each module to permit the connections. Such a complementary structural design between the different modules can more easily permit the implementation of a standard flow generator module that can optionally serve with different additional modules to become different types of respiratory treatment apparatus that provide different treatments depending on the presence of the modules.

Optionally, the housing structures of the modules of the system may also include one or more connection components to serve as a locking mechanism 116 that retains at least two modules together for operation when they are connected. For example, some embodiments may employ a set of one or more latches 116L and keepers 116K as discussed in more detail herein. The locking mechanism 116 is adapted as a portion of the structure of the housings of the modules so that when the locking mechanism 116 of two modules is aligned to engage for retaining the housings of the modules together, the gas couplings between the modules and the electrical couplers between the modules will be in the appropriate coupled position for operation.

In some cases, these locking mechanism components may be designed to be releasable so as to allow simple attachment and separation. However, they may also be designed so as to inhibit separation once they are attached. For example, they may be designed to prevent or impede certain users or patients from releasing the locking mechanism and separating the housings of the modules but permit others, such as physicians or manufacturing and maintenance personnel, to release and separate the housings.

Example Alarm Module Embodiment

Figure 7:
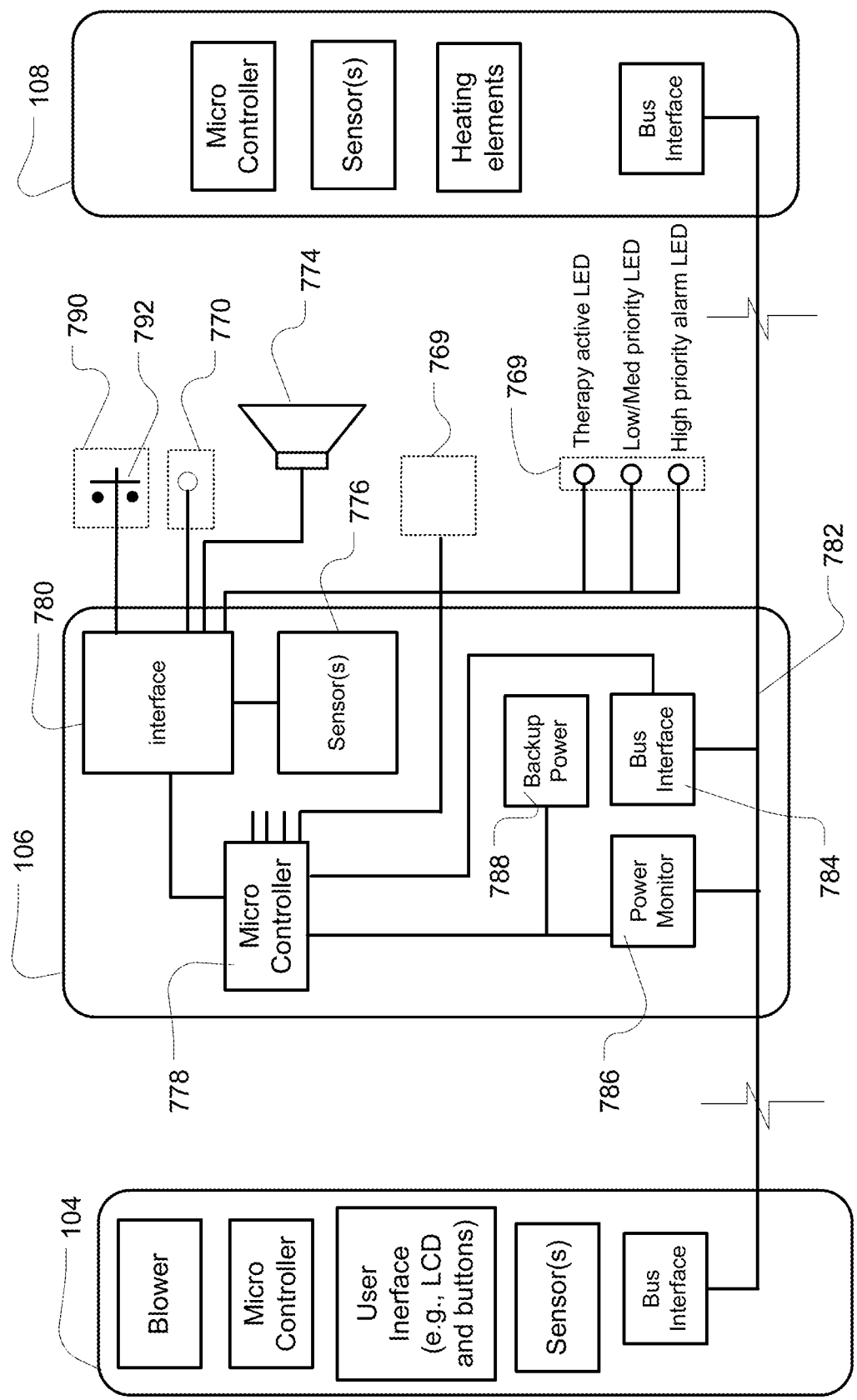
FIG. 7 is an electronic components schematic of an example arrangement of components of the modularized flow generator, alarm module and humidifier module in some embodiments of the present technology.
Figure 8A:
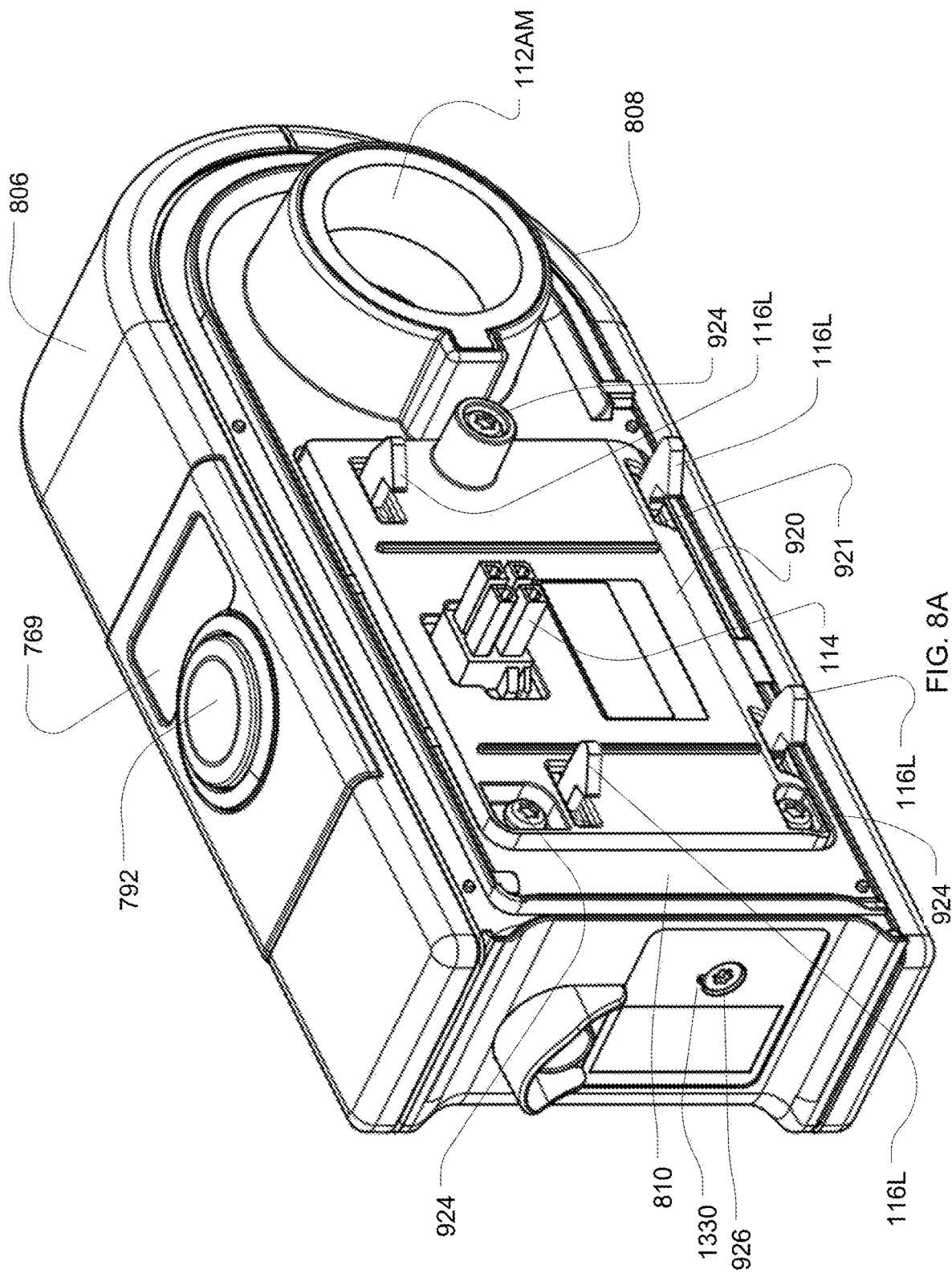
FIGS. 8A and 8B are left and right side isometric projections of an example embodiment of the modularized alarm module of the present technology.
Figure 8B:
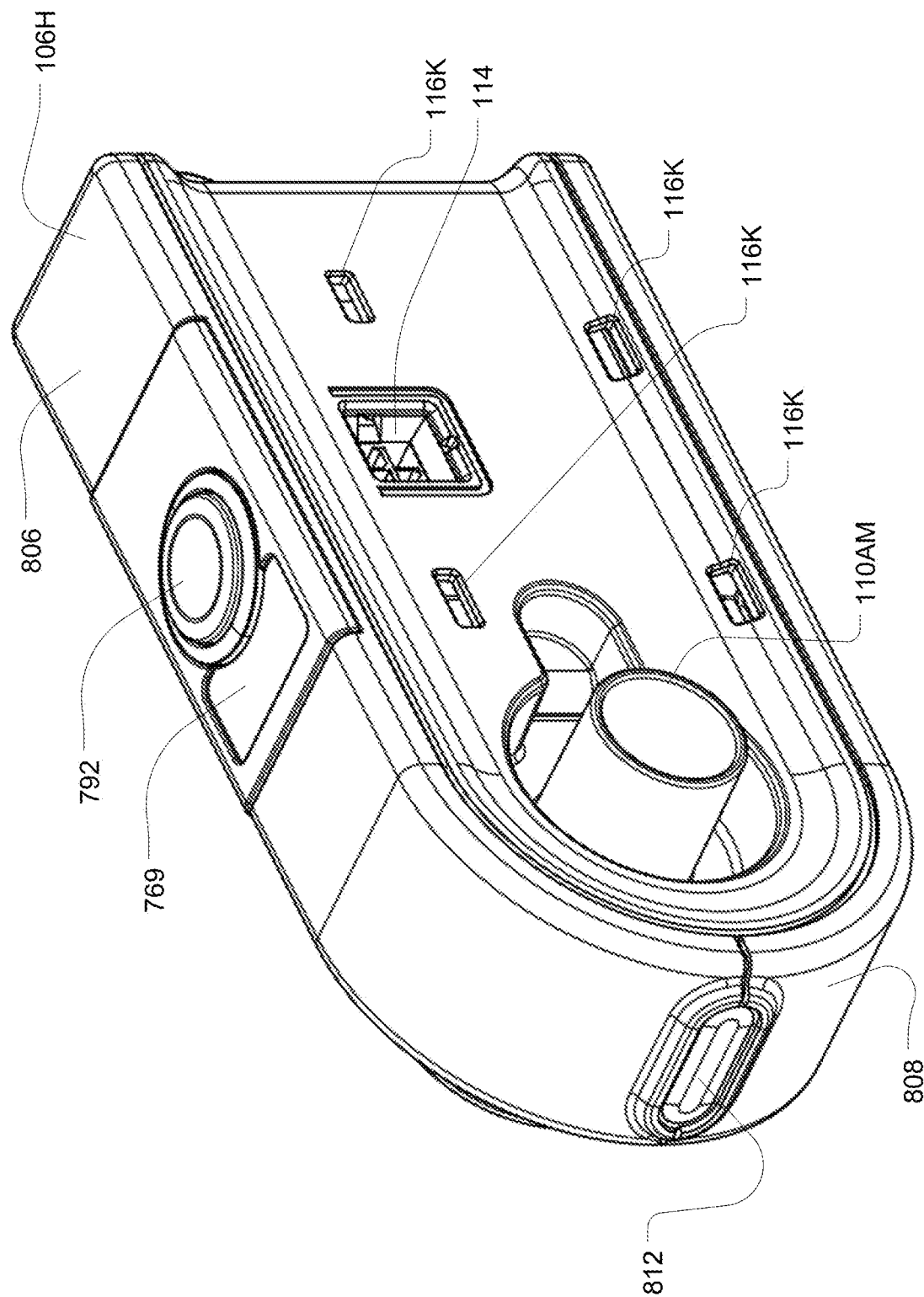
Figure 9:
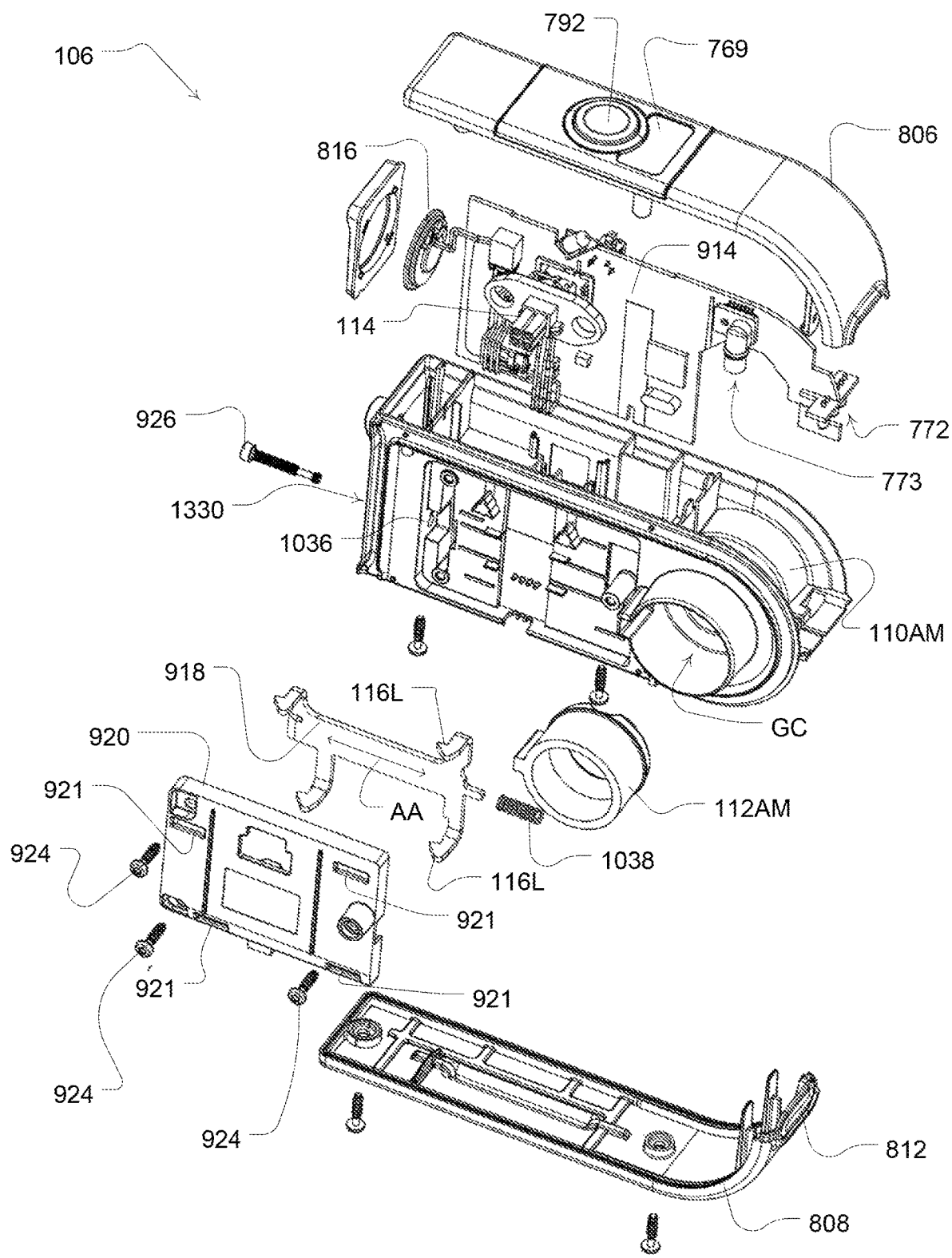
FIG. 9 is an isometric projection having an exploded view of example components of the assembly of the modularized alarm module of FIG. 8.

An example embodiment of an alarm module of the system may be further considered in reference to FIGS. 7 through 9. As schematically shown in FIG. 7, the alarm module may include several components that assist with generating alarm signals associated with the operation of a flow generator to which the module may be attached. As shown, the alarm module may include visual indicators, such as an LED or LCD, for conveying status or warning information to a user. For example, the module may optionally have an alarm display 769, such as an LCD, to present text warning messages to a user to describe a detected alarm condition and/or how to resolve or address the alarm condition. Similarly, and by way of further example, the module may also or alternatively have status lights 770 and warning lights 772. The status light may provide an indication that the alarm module is operating and functioning properly. The warning lights 772 may include a light to indicate that a treatment therapy is active or not active. The warning lights may further include an alarm light to indicate that a low and/or medium priority alarm has been triggered or not. The warning lights may also include an alarm light to indicate that a high priority alarm has been triggered or not. Optionally, to audibly convey a warning, the module may also include an audible indicator such as a loudspeaker 774.

One or more sensors 776 may also be provided in the alarm module for detecting a condition associated with a provided treatment. For example, the sensors may include a pressure sensor and/or a flow sensor (e.g., differential pressure sensor) to detect pressure and/or flow conditions in the gas channel GC of the alarm module. Optionally, a pressure sensor may be provided to sense ambient pressure or the pressure outside of the gas channel. Such a sensor may provide an ambient pressure signal to permit the alarm module or another module to determine or estimate altitude of the system or alarm module. The estimate of altitude may then be used in the control of the system, such as the setting of treatment pressure by the flow generator module. Optionally, such a sensor may generate a warning if a detected ambient pressure or altitude is not appropriate for use of the respiratory treatment apparatus.

Optionally, the sensors of the alarm module may also include a microphone to sense ambient sound or noise. For example, by sensing ambient sound or noise in the environment in which the alarm module is being utilized, the alarm module may be used for a process that sets a suitable sound level of an alarm. For example, by detecting a higher amplitude noise level in the environment in an ambient sound testing procedure with the sound sensor, a processor of the module or another module may automatically set a higher alarm output volume setting associated with a speaker of the alarm module. When a quieter environment is detected, a lower setting may be automatically set in the alarm module. For example, a selected output level for the alarm speaker may be selected by the module that is a certain threshold level above the sensed ambient sound/noise level. Such a volume setting process may be executed when the alarm module is initially powered for operation, periodically (e.g., every thirty minutes) during use of the system or in a just-in-time process that is executed by the module immediately before activation of an audible alarm but after an alarm condition has been detected.

The ambient sound sensor may also be utilized in a speaker/alarm self-testing process. For example, a processor may control activation of an audible test alarm sound through a speaker of the alarm, such as when the alarm module is initially powered. The sound sensor may then detect whether or not the alarm sounded through the speaker by sensing the alarm sound with the sound sensor. For example, an alarm tone at a known frequency may be played through the speaker and the sound sensor would generate a signal from the ambient noise of the environment including the sound of the alarm tone, which may be accessed as data by a processor. The processor may then detect whether or not the known frequency exists within the data of the signal from the sound sensor and/or whether or not the amplitude component at the detected frequency is at a suitable level. The existence of the tone and/or the existence of the tone at a sufficient magnitude would indicate that the alarm speaker is functioning. If the tone is not located in the signal by the processor or if the detected frequency does not have a sufficient magnitude, a warning may be activated by the alarm device such as a written message or a warning light. The warning may indicate that the speaker is not operating or the speaker is not operating loudly enough. Optionally, the self testing process may be conducted during use of the apparatus in response to the generation of an alarm condition as a test to ensure the alarm is sounding. Failure to sense the audible alarm may result in an alternative warning and/or shutting down the apparatus.

In some embodiments, a microcontroller 778, such as a processor, may also be included in the alarm module to control the operation of the audible indicators, the visual indicators, and/or to receive signals from the sensors via one or more interfaces 780. The microcontroller 778 may also be coupled to a bus 782 for the system as previously discussed via a bus interface 784 for communication with other modules such as sending messages and receiving messages to the other modules, such as the flow generator module, concerning status of alarm conditions or status of the alarm module. Optionally, the microcontroller 778 may monitor power with a power detector 786 coupled with the bus 782. In the event that power supplied from the bus, such as from a power source associated with the flow generator module 104 is not sufficient as detected by the power detector 786, the components of the module may be supplied with power from an optional back power source 788 such as one or more rechargeable batteries or supercapacitors.

The alarm module may also include a user input interface 790 for user control associated with the alarms. For example, the user input interface 790 may include a mute button 792 to silence an audible alarm. It may also optionally include a reset to reset an alarm. The input interface may also be implemented to set or configure the conditions associated with the alarms of the alarm module as discussed in more detail herein.

Example Alarm Module Control Methodologies

Generally, the alarm module with and/or without the flow generator module may be considered an intelligent alarm system. As such, the controller of the alarm module, either independently or depending on the additional control of another module, such as the microcontroller 796 of the flow generator module 104, will execute processing to determine the presence or absence of an alarm condition associated with the respiratory treatment apparatus and the priority of the alarm.

Thus, in some embodiments, the microcontroller 778 of the alarm module may execute prioritized alarm indications, visible and audible, and may detect alarm conditions under the control of another microcontroller of a different module, such as the controller of the flow generator which acts as a master or main controller. However, the microcontroller 778 of the alarm module may independently detect the alarm conditions and activate audio and visual alarms as well as generate signals to other modules concerning the presence and nature of the alarm. For example, a power fail condition may be detected and an associated alarm condition may be initiated by the alarm module microcontroller independently of other module's controller(s). The detection of such a condition may result in an audible and visual alarm being generated by the alarm module 106 and a signal being sent to the controller of other modules concerning the condition.

In some cases, the alarms generated by the controller of the alarm module may involve latching alarm signals that activate the audible and/or visual alarm indicators. A latching alarm signal is one that continues to be generated after its triggering event is no longer detected and may be stopped by a deliberate user action, such as the pressing of a reset button. However, some alarm signals once activated may not be easily deactivated. In such a case, some alarms may not be reset by a user. Moreover, in some embodiments, the processing of the controller(s) may be configured to permit some of the alarms conditions to be selectable or modifiable by a user or authorized clinician while some of the alarm conditions may be fixed so as to prevent disablement.

Example alarms that may be activated and/or detected with the alarm module may include a power fail condition, a high pressure or over pressure condition, a system fault (e.g., an over temperature condition, a blocked tube of a patient interface or blocked gas channel, disconnected patient interface or tube thereof, a humidifier lid open, a high leak or Mask Off condition), a non-vented mask condition, a Low pressure settable condition, a high pressure settable condition, a low minute ventilation condition, a apnea condition and/or a sensor failure condition, etc. Whether detected by the alarm module or controller of another module, the controller of the alarm module will generate the audible and/or visual alarms associated with these conditions in the alarm module with the visual and/or audible indicators of the alarm module. In the case that the condition is detected by the controller of another module, the detecting module will transmit a signal on the bus to the alarm module. When the controller of the alarm module receives the signal, the controller of the alarm module will then generate the appropriate audible and/or visual alarms based on the type of alarm message received on the bus.

Additional example conditions that may be assessed by one or more controllers for detecting the above listed alarms may be as follows:

(1) a power fail condition: no power or insufficient power is detected while the flow generator is delivering a pressure treatment.

(2) a high pressure or over pressure condition: a sensed pressure is greater than a pressure threshold (e.g., 25 or 30 depending on the detected type of flow generated module attached) for a time period exceeding a time threshold (e.g., 0.7 seconds).

(3) an over temperature condition: a temperature detected by a thermister associated with a controller of any attached module has exceeded a temperature threshold.

(4) a blocked tube of a patient interface or blocked gas channel: a measure of patient flow is below a flow threshold (e.g., 12 liters per minute) and a measure of pressure is above a pressure threshold (e.g., 10 cmH$_2$O) for a period of time exceeding a time threshold (e.g., in a range of about 30 to 50 seconds, such as 40 seconds).

(5) a disconnected patient interface or tube thereof: this condition may be detected when a measure of pressure is less than a pressure threshold (e.g., 2 cmH$_2$O) and a measure of blower speed is above a speed threshold (e.g., 8955 revolutions per minute) for a period of time exceeding a time threshold (e.g., 1 second).

(6) a humidifier lid open: the presence of the humidifier module is detected and a lid sensor is detected as being open or a measure of pressure is detected below a pressure threshold (e.g., 3.5 cmH$_2$O) and a measure of flow is detected as being over a flow threshold (e.g., 120 liters per minute) for a time exceeding a time threshold (e.g., 5 seconds).

(7) a high leak or Mask Off condition: a measure of leak exceeds a leak threshold (e.g., 40 liters/minute) for a time period exceeding a time threshold (e.g., 20 seconds). A controller may deactivate this alarm when the measure of leak falls below the leak threshold for a period of time (e.g., 6 seconds.)

(8) a non-vented mask condition: this condition may be detected when flow generator is determined to be generating a pressure treatment for a non-vented mask and a measure of leak falls below a leak threshold (e.g., −7.5 liters per minute) for a period of time that exceeds a time threshold (e.g., 10 seconds). A controller may deactivate this alarm when the measure of leak is above a leak threshold (e.g., 7.5 liters per minute) for a period of time (e.g., 30 seconds.)

(9) a Low pressure settable condition: this condition may be detected when a measure of pressure is less than a pressure treatment setting by some user-configured amount (e.g., 0 to 10 cmH$_2$O) for a period of time exceeding a time threshold (e.g., 12 seconds). A controller may deactivate this alarm when the measure of pressure satisfies the pressure treatment setting for a period exceeding a time threshold (e.g., 100 milliseconds).

(10) a high pressure settable condition: this condition may be detected when a measure of pressure is higher than a pressure treatment setting by some user-configured margin (e.g., 0 or 4 to 35 cmH$_2$O) for a period of time exceeding a time threshold (e.g., 7 seconds). A controller may deactivate this alarm when the measure of pressure satisfies the pressure treatment setting for a period exceeding a time threshold (e.g., 100 milliseconds).

(11) a low ventilation condition: this condition may be detected when a measure of ventilation (e.g., a minute ventilation) falls below a configurable ventilation threshold (e.g., 1 to 20 liters per minute). A controller may deactivate this alarm when the measure of ventilation satisfies the ventilation threshold for a period of time exceeding a time threshold (e.g., 30 seconds).

(12) an apnea condition: this condition may be detected when there are no breaths detected within a time period exceeding a configurable time threshold (e.g., 5 to 45 seconds). A controller may deactivate this alarm when a number of spontaneous breaths (e.g., 3) are detected in the time period.

(13) a sensor failure condition (e.g., pressure transducer): this condition may be detected if the flow generator module is generating a pressure treatment (e.g., is in run mode) and if a measure of pressure is less then a pressure threshold (e.g., 1 cmH$_2$O) for over a period of time exceeding a time threshold (e.g., 5 seconds). Other alarm conditions may also be implemented.

(14) Oximeter Sensor Failure: this condition may be detected if a flow generator module fails to detect a connection to an oximeter module when the flow generator treatment mode is configured to use an oximeter. The detection of the absence of the oximeter may result in activation of an alarm through the alarm module such as a message on an LCD, a warning light or LED and/or an audible warning sound via a sound generator (e.g., a warning tone or an audible voice message advising a user to connect an oximeter).

(15) Oximeter Dislodged Condition: This condition may be detected if an oximeter module detects that an oximeter finger sensor has fallen off a patient's finger. For example, a pulse oximeter module may detect the dislodged sensor and send a message to an alarms module via a flow generator module. The detection of the dislodged sensor may result in activation of an alarm of the alarm module such as a message on an LCD, a warning light or LED and/or an audible warning sound via a sound generator (e.g., a warning tone or an audible voice message advising a user to wear the sensor).

(16) Blood Gas Condition: This condition may be detected if a measured blood gas, such as a blood gas measured by an oximeter module, does not meet a threshold. For example, if a low oxygen level is detected, such as if PaO$_2$ falls below a percentage threshold (e.g., 85%). The detection of the dislodged sensor may result in activation of an alarm of the alarm module, such as in response to a communication from the flow generator module. The alarm activated in the alarm module may be a message on an LCD, a warning light or LED and/or an audible warning sound via a sound generator (e.g., a warning tone or an audible voice message advising a user of a low blood gas condition).

(17) A Back-up Power Source Warning: This condition may be detected if the back-up power source of the module does not meet required performance requirements such as holding sufficient power for back-up operations. For example, in the case of a supercapacitor, the microcontroller may generate an early warning signal by detecting a decrease in the capacitance of the supercapacitor. In such a case, the microcontroller of the alarms module may monitor the charging and/or discharging rate of the supercapacitor during main power on/off and determine the approximate capacitance of the supercapacitors. An alarm may be generated if the determined capacitance does not meet a predetermined threshold. Other methods for testing the back-up power may also be implemented and may depend on the type of back-up source. The alarm activated in the alarm module may be a message on an LCD, a warning light or LED and/or an audible warning sound via a sound generator (e.g., a warning tone or an audible voice message advising a user to seek service of the back-up power source.)

The following Table A identifies whether some of the previously described alarm conditions have settings (e.g., configurable thresholds for the conditions and/or whether the alarm conditions may be enabled/disabled) that may be adjusted or configured by a user and/or clinician and whether the alarms may be reset once they have been triggered for an example embodiment.

TABLE A

| Alarm | Configurable | Resetable |
|---|---|---|
| Power Fail | N | N |
| Over Pressure | N | N |
| System Fault | N | N |
| Over temperature | N | N |
| Blocked tube | N | N |
| Humidifier lid open | N | N |
| High Leak/Mask Off | Y | Y |
| Non-Vented Mask | Y | Y |
| Low Pressure settable | Y | Y |
| High Pressure settable | Y | Y |
| Low minute Ventilation | Y | Y |
| Apnea | Y | Y |
| Sensor Failure | N | N |

Example Alarm Sound Signal

One aspect of one form of the present technology is an alarm that uses frequency synthesizing to achieve the alarm spectrum. One example of an alarm sound signal is to use a microcontroller to synthesize a complex frequency signal that contains a fundamental frequency and four harmonic sound frequencies. A digital to analog converter (DAC) may then be used to produce the required sound signal. An example methodology for producing the sound signal is as follows:

1. Choose a fundamental frequency $F_0$; let $\omega_0 = 2\pi F_0$;
2. Compose a sound signal:

$$S(t) = k1 \sin(\omega_0 t + \phi_1) + k2 \sin(2\omega_0 t + \phi_2) + k3 \sin(3\omega_0 t + \phi_3) + k4 \sin(4\omega_0 t + \phi_4) + k5 \sin(\omega_0 t + \phi_5)$$

where:
k1 ... k5 are the amplitude coefficients that will be used to fine tune the sound pressure level of the harmonics;

$\phi_1$ ... $\phi_5$ are the initial phase shift for individual frequency components. The defaults of the amplitude coefficients may be set to 1; the default phase shifts may be set to 0°. These coefficients can be tuned as desired.

3. Sample the sound signal S(t) at a rate of $SR = 32 \times 5 F_0$ for a period of $T = 1/F_0$; start from t=0;
4. Convert the sampled data, such as to an 8-bit DAC dataset for a digital to analog converter of the microcontroller of the alarm module:

$$DATA(n) = 128 + \frac{250 \times S(t_n)}{\text{Max}(S(t)) - \text{Min}(S(t))}$$

In one form of the present technology, an alarm speaker is driven by a switching mode audio driver, for example, a class D amplifier (PWM modulated by synthesized signal). An advantage of this approach is that it is a high efficiency amplifier, for example with an electrical efficiency of 90% or greater. By way of comparison, a class C linear amplifier may have an electrical efficiency of less than 50%. This high efficiency amplifier does not need additional storage capacitor and provides a very wide output volume adjustment range.

Example Alarm Module Structure

The modularized housing structure of the alarm module may be considered in more detail in reference to FIGS. 8A, 8B and 9. In this embodiment, the components of the alarm module housing 106H include an upper case 806, a lower case 808 and a housing support 810. The upper case 806 serves as a panel for the mute button 792 and may also include a panel which may be for a label for the mute button or may optionally be for an LCD-type alarm display 769 in some embodiments. The lower case 808 serves as a base for the alarm module and may include a window 812 for warning lights 772.

The housing support 810, to which the lower case and upper case of the housing may be attached, contains an electronics board 914 for the previously described electronics components of the module (e.g., the microcontroller, bus, sensors, lights, interface for speaker 816 etc.). For example, a sensor coupling 773 may be included for coupling of a pressure sensor to a gas channel of the module. In such a case the coupling may be connected with a pressure sensor attached to the electronics board 914 and the coupling permits the pressure sensor to seal with the gas channel for sensing pressure in the gas channel. The housing support 810 is also formed so as to include the gas channel GC. The gas couplings (e.g., input coupling 112AM) may attach to the gas channel GC of the housing support 810 such as by an interference fit or may be formed as part of the housing support such as in the case of the output coupling 110AM. Similarly, the electrical coupler 114 is attached to the housing support 810 and wired to the electronics board 914 which includes wiring for the bus. The electrical coupler may be either a male plug or female receptacle version. In the version of FIG. 8A, a male plug of the alarm module may be inserted into a female receptacle of the flow generator module. Optionally, the alarm module may include an electrical coupler of the female receptacle version (shown in FIG. 8B) on the opposing side of the alarm module into which a male plug of the humidifier module may be inserted.

A latching element 918 of the locking mechanism 116 including latches 116L is attached to the housing support 810 with latch retainer 920 and retainer screws 924 so as to hold the latching element 918 against the housing support 810 but permit the latching element to traverse laterally under the retainer for a latching movement. The latch retainer 920 includes latch slots 921 in which the latches may move. The lateral movement of the latching element, and particularly the latches 116L, permits the latches 116L to move to an engagement position EP and disengagement position DP to engage or disengage with engagement apertures or keepers 116K of another module structure (e.g., a flow generator module) to which the alarm module may be attached.

Figure 10:
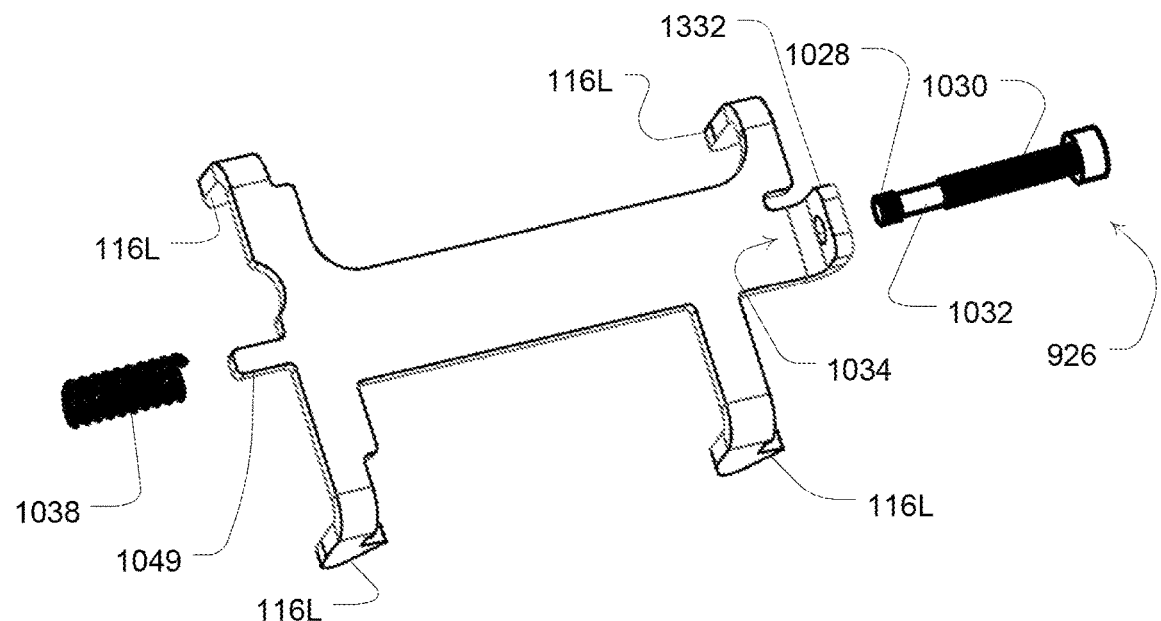
FIG. 10 is a three dimensional drawing of some components of a locking mechanism for a module of a respiratory treatment apparatus of the present technology.
Figure 10A:
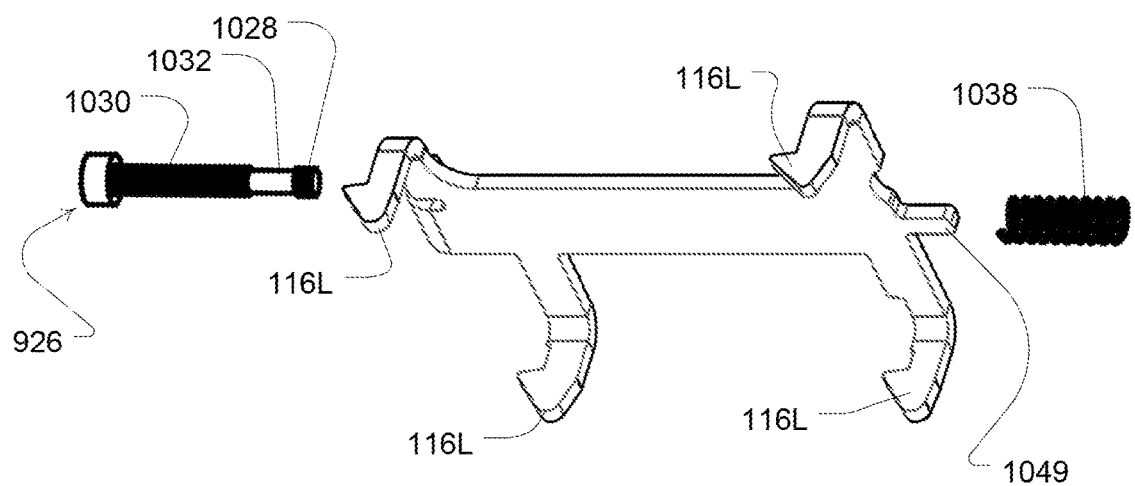
FIG. 10A is another view of the components of the locking mechanism of FIG. 10.

A securing shaft 926 is provided for selectably securing and releasing the latching element 918 to permit or prevent its lateral movement under the retainer in a direction indicated by line AA of FIG. 9. As illustrated in more detail in FIGS. 10 and 10A, the securing shaft 926, which may for example include a screw head or bolt head, may include multiple threaded portions, such as first threaded portion 1028 and second threaded portion 1030 separated by a blank or unthreaded shaft portion 1032. In an alternative form, securing shaft 926 may have a single threaded portion. The threaded portions are sized for a threaded aperture 1034 integrated with the latching element 918. When assembled, the securing shaft 926 may be inserted within or through a housing aperture 1036, which may be unthreaded, of the alarm module housing 106H or housing support 810 to engage with the threaded aperture 1034 of the latching element. A biasing element 1038, such as a spring, may be provided to bias the latching element to a particular position along its lateral movement path. For example, as discussed in more detail with regard to FIG. 12, the biasing element may bias the latching element such that the latches will automatically engage in a locked position when inserted or engaged with the engagement apertures or keepers 116K of another module. When a spring is implemented, the latching element 918 may include a spring mount 1049 for attaching the spring to the latching element 918.

Figure 11:
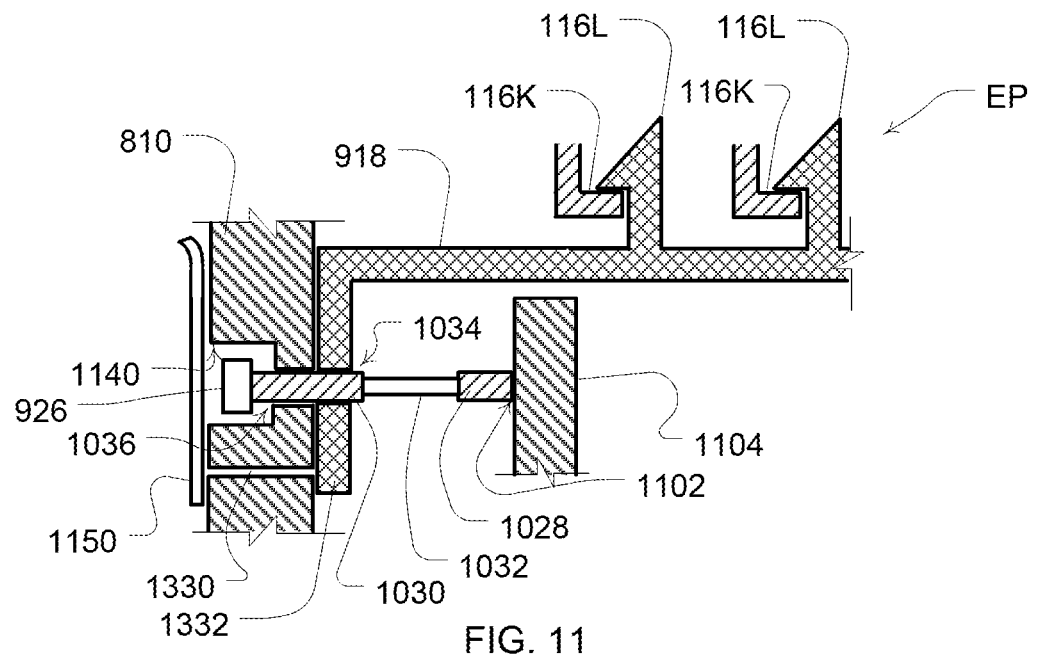
FIG. 11 is a cross sectional view of a latching structure of an example locking mechanism of the present technology showing the locking mechanism in secured and engaged position.

The components of the locking mechanism can provide a tamper resistant means for releasably locking two modules together, such as the alarms module and the flow generator module of a respiratory treatment apparatus. The tamper resistant operation of the locking mechanism may be considered in reference to FIGS. 11 through 14. In FIG. 11, the second threaded portion 1030 is engaged with the threaded aperture 1034 of the latching element 918 so as to secure the latching element from movement such as by retaining it against a portion of the housing support 810. In this position, the latching element 918 is locked from movement as the shaft end 1102 of the securing shaft 926 plies against a shaft stop 1104 of the housing support 810 to force the latching element 918 against the housing support 810 when the securing shaft is threaded into the latching element 918. Thus, the latches 116L of the latching element will remain engaged with the keepers 116K or engagement apertures of another module in which they have been inserted and prevent the module from being separated. Optionally, the housing support 810 may include a raised aperture ridge 1140 surrounding the housing aperture 1036. The aperture ridge 1140 may conceal the head of the securing shaft 926 below the ridge when the securing shaft locks the latching element. In such a case, an optional security label 1150 or sticker may be applied or adhered to the housing support over the aperture ridge 1140 and the securing shaft 926 that is positioned beneath the ridge. Tampering with or removal of the label 1150 may serve as an indication of unauthorized access to the securing shaft 926 and unauthorized separation of the modules locked by the locking mechanism.

Figure 12:
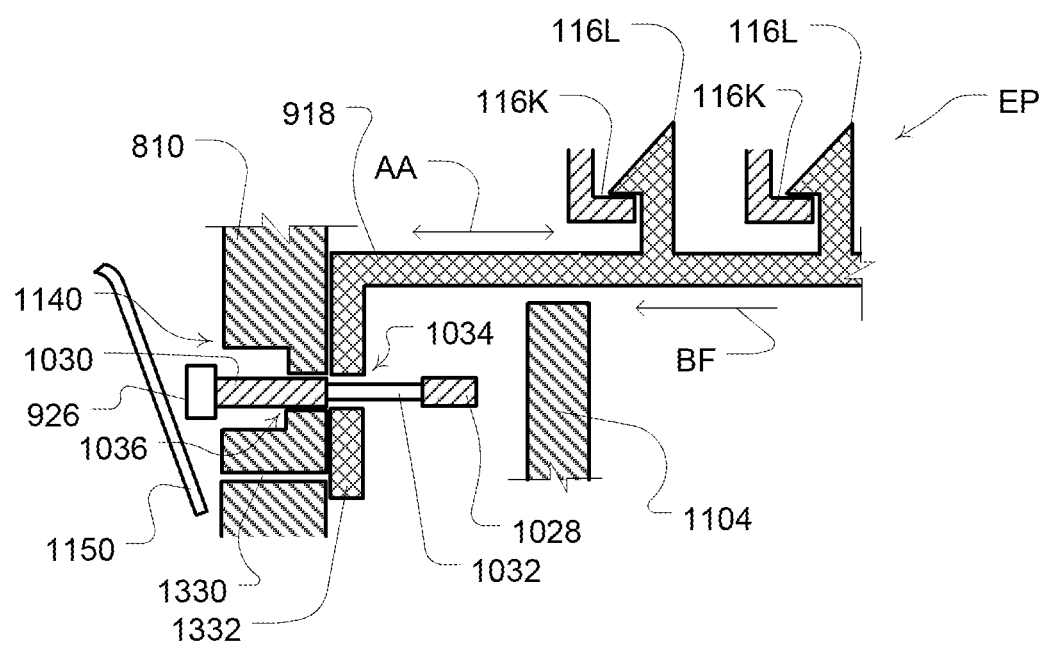
FIG. 12 is a cross sectional view of the latching structure of the locking mechanism of FIG. 11 showing the locking mechanism in unsecured, biased and engaged position.

In FIG. 12, the locking mechanism remains locked due to the bias of the biasing element 1038 (not shown in FIG. 12) which may provide a biasing force BF to bias the latching element 918 against the housing support 810 even when the securing shaft has been unthreaded from the threaded aperture 1034 of the latching element 918. In this biased position, the latches 116L are still in the engaged position EP with respect to any engagement aperture or keeper 116K of another module. Due to the structure of the alarm module housing 106H, when the module is attached to another module, the latching element or latches are not readily accessible to move the latching element 918 into its disengagement position DP.

Figure 13:
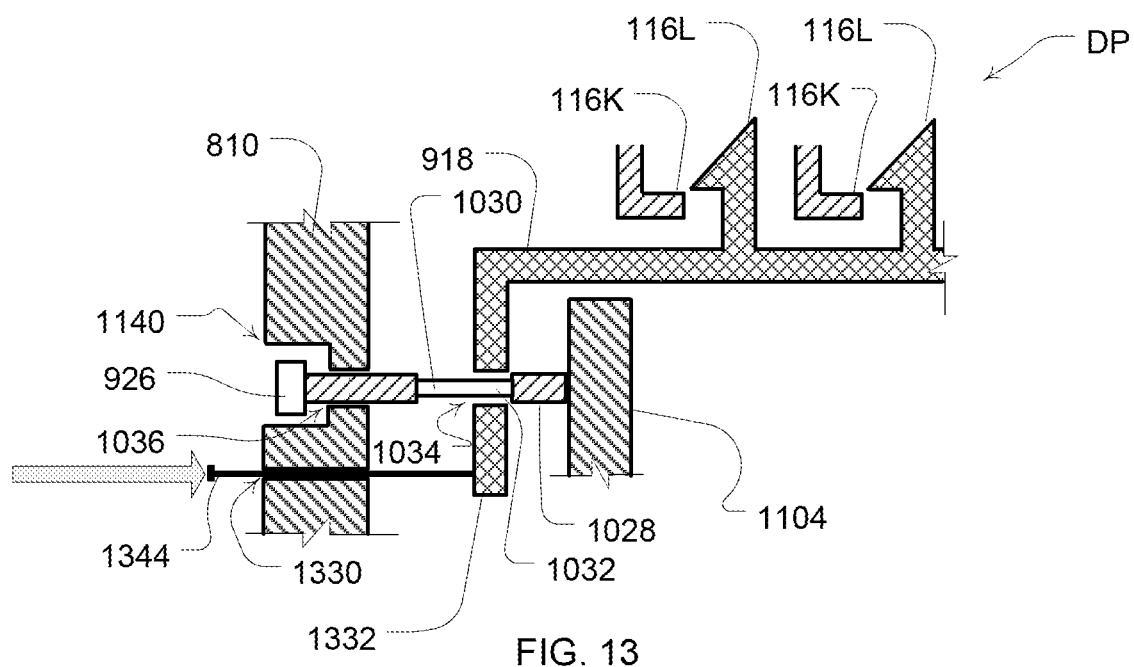
FIG. 13 is a cross sectional view of the latching structure of the locking mechanism of FIG. 11 showing the locking mechanism in a disengaged position.

In this regard, the alarm module housing 106H protects against or conceals access to the latching element 918 and may provide only limited access to it. For example, a small release port 1330, such as a pin hole that may be covered by the label 1150, may be provided to access and move the latching element 918 when it is unthreaded from the securing shaft as illustrated in FIG. 13. The latching element overlaps the release port 1330 such as at an optional tail portion 1332 of the latching element 918. When applying a rigid wire or pin 1344 sized to pass through the release port 1330, the wire or pin can ply against the latching element, such as at the tail portion 1332, to counteract the biasing force and laterally move the latching element to its disengagement position DP. This lateral movement is permitted because the unthreaded shaft portion 1032 does not restrict lateral movement of the latching element. In other words, the threaded aperture 1034 of the latching element 918 can traverse along the unthreaded shaft portion 1032, and may do so without rotation of the shaft portion due to the smaller diameter of the unthreaded shaft portion relative to the first and second threaded portions and the threaded aperture 1034, in order to move between the engaged position and the disengaged position. Due to the biasing force provided by the biasing element 1038 of the latching element 918, when the pin or wire is removed, the latching element 918 will return to its engaged position.

Figure 14:
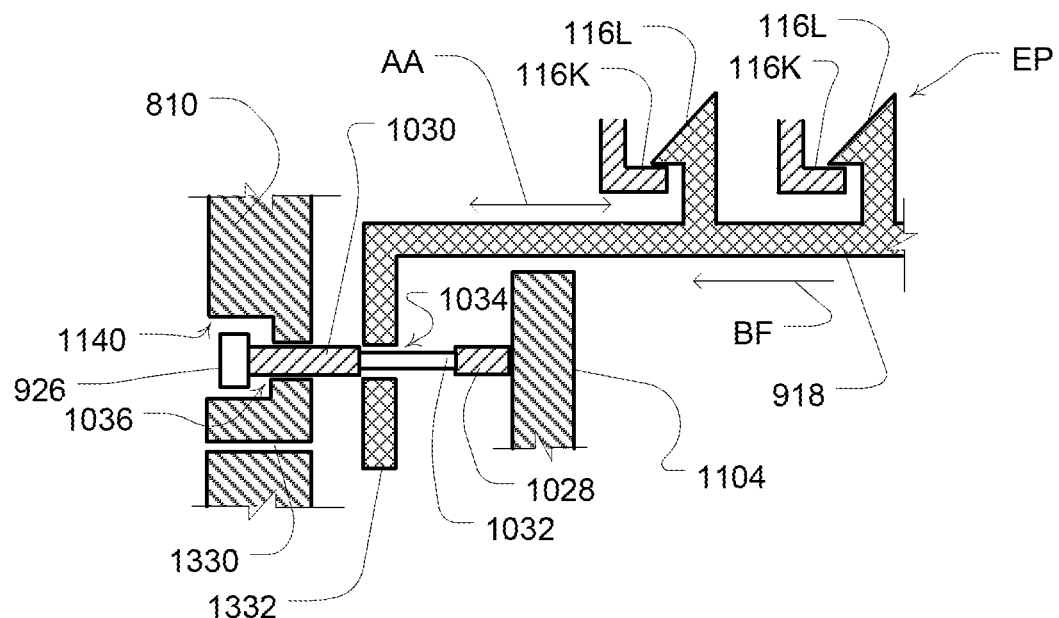
FIG. 14 is a cross sectional view of the latching structure of the locking mechanism of FIG. 11 showing the locking mechanism in a engaged position.

As shown in FIG. 14, the particular location of the shaft stop 1102 and size of the threaded portions and securing shaft 926, allows the securing shaft to be tightened into the threads of the threaded aperture of the latching element when the securing shaft is pressed inwards toward the latching element 918 because the biasing force of the biasing element pushes the latching element against the second threaded portion 1030. However, it does not allow a pressing against the securing shaft 926 to move the latching element 918 into its disengaged position from its engaged position even when the securing shaft 926 is unthreaded from the latching element 918. In this regard, the distance which the securing shaft 926 may be pressed inward toward the shaft stop 1102 is not sufficient for the end of the second threaded portion 1030 to push the latching element to its disengaged position DP.

In the foregoing description and in the accompanying drawings, specific terminology, equations and drawing symbols are set forth to provide a thorough understanding of the present technology. In some instances, the terminology and symbols may imply specific details that are not required to practice the technology. For example, although the terms "first" and "second" have been used, unless otherwise specified, they are not intended to indicate any order but may be utilized to distinguish between distinct elements. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology. For example, as previously discussed, in some embodiments the components within the housing of the alarm module may include a controller with a processor to control alarms with alarm components (e.g., speaker, lights, LEDs, LCD etc.) that produce warning and alarms in the alarm module. However, in some embodiments, such a controller or processor may be in other modules, such as the flow generator module. In such a case, the alarm module need not include a controller but may include the alarm components that electronically couple to a controller of another module.

Moreover, while the illustrated alarms module includes a housing that serves as an external casing to retain the components of the module, in some embodiments the alarm components of the module may be configured as an alarms card that may be inserted within another module, such as inside the housing of the flow generator module. In such a case, the alarms card may include the aforementioned components and functions of the alarms module. However, the card may be docked with electrical and gas connections on a mother board within the housing of the flow generator, such as if the housing of the flow generator is configured to open and close. In such a case, the housing of the flow generator module can serve as an external casing for the alarms card as well as the flow generator. Such an alarms card may or may not have an independent housing of its own.

Still further, and as contemplated and previously described herein, the modules may be coupled together with certain tamper resistant locking features as described in more detail herein. Thus, modules of any functionality may be coupled together with such features. For example, in addition to being integrated with an alarms module or a flow generator module, the tamper resistant locking features may be implemented with one or more modules such as a wired and/or wireless communications module that permits electronic data and instructions to be transferred to and from the system or flow generator such as via network communications. For example, a person may "daisy chain" one or more additional modules to a respiratory treatment apparatus. Other module examples include a docking interface module, such as one that permits easy electronic docking of other user devices to the respiratory system so that they may operate and communicate with the system (e.g., a music player dock, a LCD display dock, a smart phone dock, an electronic personal data assistant dock etc.).

In an alternative configuration, the one or more modules may be connected to the top, bottom, front or back of the respiratory treatment apparatus, or any combination thereof. In an alternative configuration, the one or more modules may be connected to an interior portion of the respiratory treatment apparatus.

One of the advantages of one form of the present technology, where there are separate therapy and mitigation modules, is a reduced product development time. Another advantage of one form of the present technology, where there are separate therapy and mitigation modules, is improved manufacturing efficiencies.

Despite the complexity of a speaker when compared to a buzzer, and the more complicated manufacture procedure for including a speaker, implementation of a speaker is preferred in the present technology. An advantage of the use of a speaker in accordance with the present technology is the improved electrical efficiency, which can lead to reduced power requirements and reduced physical size of a corresponding supercapacitor.

A further advantage of one form of the present technology is that it improves the safety of a respiratory apparatus by making it difficult for a patient to inadvertently remove a safety feature, e.g. an alarm module, in those situations where it may be important for such an additional module to remain connected once it has been added to the respiratory treatment apparatus.

| Reference signs list | |
|---|---|
| Part References | Numbers |
| respiratory treatment apparatus | 102 |
| flow generator module | 104 |
| flow generator housing | 104H |
| alarm module | 106 |
| alarm module housing | 106H |
| humidifier module | 108 |
| humidifier housing | 108H |
| output coupling | 110AM |
| breathable gas output coupling | 110FG |
| electrical coupler | 114 |
| locking mechanism | 116 |
| keepers | 116K |
| latches | 116L |
| alarm display | 769 |
| status lights | 770 |
| warning lights | 772 |
| sensor coupling | 773 |
| loudspeaker | 774 |
| sensors | 776 |
| microcontroller | 778 |
| interfaces | 780 |
| bus | 782 |
| bus interface | 784 |
| power detector | 786 |
| optional back power source | 788 |
| user input interface | 790 |
| mute button | 792 |
| upper case | 806 |
| case | 808 |
| housing support | 810 |
| window | 812 |
| speaker | 816 |
| electronics board | 914 |
| latching element | 918 |
| latch retainer | 920 |
| latch slots | 921 |
| retainer screws | 924 |
| shaft | 926 |
| threaded portion | 1028 |
| threaded portion | 1030 |
| unthreaded shaft portion | 1032 |
| aperture | 1034 |
| housing aperture | 1036 |
| biasing element | 1038 |
| spring mount | 1049 |
| shaft stop | 1102 |
| aperture ridge | 1140 |
| label | 1150 |
| release port | 1330 |
| small release port | 1330 |
| tail portion | 1332 |
| pin | 1344 |

The invention claimed is:

1. A tamper resistant locking mechanism for releasably coupling discrete modules of a treatment apparatus, the locking mechanism comprising:
   a movable latching portion, the movable latching portion being adapted for engagement with engagement apertures of a first housing structure; and a securing shaft configured to secure the latching portion, the securing shaft comprising first and second sets of threads and an unthreaded shaft portion, the first and second sets of threads being separated by the unthreaded shaft portion.

2. The locking mechanism of claim 1 wherein the latching portion comprises a threaded aperture for the securing shaft, the latching portion adapted to be secured against a second housing structure by coupling the second set of threads and threaded aperture so as to prevent displacement of the latching portion from the engagement apertures.

3. The locking mechanism of claim 2 wherein the threaded aperture of the latching portion is adapted for slideable engagement with the unthreaded portion of the securing shaft to permit the latching portion to be moved for releasing and catching the latching portion.

4. The locking mechanism of claim 2 wherein the second housing structure comprises a release aperture, the release aperture positioned and sized to selectively permit access to the latching portion to displace the latching portion for releasing the latching portion from the engagement apertures.

5. The locking mechanism of claim 2 wherein the second housing structure comprises an shaft aperture for receiving the securing shaft and engaging the securing shaft when the latching portion is secured against the second housing structure with the second set of threads of the securing shaft.

6. The locking mechanism of claim 5 further comprising a security label to conceal the shaft aperture.

7. The locking mechanism of claim 6 wherein the securing shaft comprises a screw.

8. The locking mechanism of claim 2 wherein the first housing structure comprises a housing to retain a flow generator of a respiratory treatment apparatus and wherein the second housing structure comprises a housing to retain an alarms module for the respiratory treatment apparatus.

* * * * *